(12) United States Patent
Burja et al.

(10) Patent No.: US 8,765,422 B2
(45) Date of Patent: Jul. 1, 2014

(54) D4 DESATURASES AND D5 ELONGASES

(75) Inventors: Adam Burja, Palo Alto, CA (US); Gabrielle S. Chafe, Toronto (CA); Helia Radianingtyas, Palo Alto, CA (US)

(73) Assignee: DSM Nutritional Products AG, Kaiseraugst (CH)

( * ) Notice: Subject to any disclaimer, the term of this patent is extended or adjusted under 35 U.S.C. 154(b) by 797 days.

(21) Appl. No.: 12/668,793

(22) PCT Filed: Oct. 31, 2007

(86) PCT No.: PCT/IB2007/004553
§ 371 (c)(1),
(2), (4) Date: Jun. 17, 2010

(87) PCT Pub. No.: WO2009/010825
PCT Pub. Date: Jan. 22, 2009

(65) Prior Publication Data
US 2011/0059494 A1    Mar. 10, 2011

Related U.S. Application Data

(60) Provisional application No. 60/949,730, filed on Jul. 13, 2007.

(51) Int. Cl.
*C12P 7/64* (2006.01)

(52) U.S. Cl.
USPC .......... 435/134; 435/7.1; 435/183; 435/254.2; 435/320.1

(58) Field of Classification Search
None
See application file for complete search history.

(56) References Cited

U.S. PATENT DOCUMENTS

| | | | |
|---|---|---|---|
| 6,635,451 B2 | 10/2003 | Mukerji | 435/71.1 |
| 7,070,970 B2 | 7/2006 | Mukerji | 536/23.2 |
| 7,736,884 B2 * | 6/2010 | Gunnarsson et al. | 435/254.1 |
| 7,842,852 B2 | 11/2010 | Cirpus | 800/278 |
| 8,134,046 B2 | 3/2012 | Cirpus | 544/157 |
| 2009/0222951 A1 | 9/2009 | Cirpus | 800/281 |

FOREIGN PATENT DOCUMENTS

| | | |
|---|---|---|
| WO | WO 02/26946 | 4/2002 |
| WO | WO 03/078639 | 9/2003 |
| WO | WO 2005/083093 | 9/2005 |
| WO | WO 2005/103253 | 11/2005 |
| WO | WO 2005/118814 | 12/2005 |
| WO | WO 2006/008099 | 1/2006 |
| WO | WO 2006/064317 | 6/2006 |
| WO | WO 2007/017419 | 2/2007 |
| WO | WO 2007/069078 | 6/2007 |

OTHER PUBLICATIONS

U.S. Appl. No. 60/751,401, filed Dec. 16, 2005.
U.S. Appl. No. 60/821,084, filed Aug. 1, 2006.
Burja AM, et al. (2006) Isolation and characterization of polyunsaturated fatty acid producing *Thraustochytrium* species: screening of strains and optimization of omega-3 production. Appl Microbiol Biotechnol. 72(6): 1161-1169.
GenBank Accession No. AAZ43257 (delta-4 fatty acid desaturase—*Thraustochytrium* sp. FJN-10); retrieved on Feb. 11, 2009 at www.ncbi.nlm.nih.gov/entrez/viewer.fcgi?db=protein&id=71842217 (2 pages).
GenBank Accession No. CAP40234 (unnamed protein product from *Thraustochytrium* sp.), print out retrieved on Nov. 13, 1999 at www.ncbi.nlm.nih.gov/sites/entrez?cmd=Retrieve&db=protein&dopt=GenPept&RI . . . (1 page).
GenBank Accession No. Q2PWB8 (polyunsaturated fatty acid elongase 1), print out retrieved Feb. 11, 2009 at www.ncbi.nlm.nih.gov/entrez/viewer.fcgi?db=protein&id=122202565 on (1 page).
Okuley J, et al. (1994) *Arabidopsis* FAD2 gene encodes the enzyme that is essential for polyunsaturated lipid synthesis. Plant Cell. 6(1): 147-158.
Qiu X, et al. (2001) Identification of a Delta 4 fatty acid desaturase from *Thraustochytrium* sp. involved in the biosynthesis of docosahexanoic acid by heterologous expression in *Saccharomyces cerevisiae* and *Brassica juncea*. J Biol Chem. 276(34): 31561-31566.
International Preliminary Report on Patentability mailed Apr. 22, 2010 for PCT/IB2007/004553 filed on Oct. 31, 2007 and published as WO 2009/010825 on Jan. 22, 2009 (Applicant—Ocean Nutrition Canada Ltd. // Inventors—Burja et al.) (9 pages).
International Search Report and Written Opinion mailed on Feb. 13, 2009 for PCT/IB2007/004553 filed on Oct. 31, 2007 and published as WO 2009/010825 on Jan. 22, 2009 (Applicant—Ocean Nutrition Canada Ltd. // Inventors—Burja et al.) (18 pages).
Application to Amend a Complete Specification filed on Jan. 25, 2011 for South African Application No. 2010/01405, which claims priority to PCT/IB2007/004553 filed on Oct. 31, 2007 (Applicant—Ocean Nutrition Canada Ltd. // Inventors—Burja et al.) (13 pages).
Amended Claim Set filed Oct. 29, 2010 for Japanese Patent Application No. 2010-516603, which claims priority to PCT/IB2007/004553 filed on Oct. 31, 2007 (Applicant—Ocean Nutrition Canada Ltd. // Inventors—Burja et al.) (4 pages).
Response to Office Action filed Feb. 13, 2012 for Mexican Patent Application No. MX/a/2010/000548, which claims priority to PCT/IB2007/004553 filed on Oct. 31, 2007 (Applicant—Ocean Nutrition Canada Ltd. // Inventors—Burja et al.) (2 pages).
Official Action mailed Nov. 15, 2011 for Mexican Patent Application No. MX/a/2010/000548, which claims priority to PCT/IB2007/004553 filed on Oct. 31, 2007 (Applicant—Ocean Nutrition Canada Ltd. // Inventors—Burja et al.) (2 pages).
Request for Examination filed Mar. 28, 2012 for Australian Patent Application 2007356650, which claims priority to PCT/IB2007/004553 filed on Oct. 31, 2007 (Applicant—Ocean Nutrition Canada Ltd. // Inventors—Burja et al.) (10 pages).

(Continued)

*Primary Examiner* — Hope Robinson
(74) *Attorney, Agent, or Firm* — Kilpatrick Townsend & Stockton LLP

(57) ABSTRACT

Disclosed are methods and compositions related to ONC-T18, D4-desaturases, D5 elongases, their isolation, characterization, production, identification, and use for fatty acid production, as well as organisms containing these compositions and organisms expressing them.

16 Claims, 4 Drawing Sheets

(56) References Cited

OTHER PUBLICATIONS

Direction to Request Examination filed Dec. 20, 2011 for Australian Patent Application 2007356650, which claims priority to PCT/IB2007/004553 filed on Oct. 31, 2007 (Applicant—Ocean Nutrition Canada Ltd. // Inventors—Burja et al.) (1 page).

Request for Examination filed Nov. 14, 2011 for Canadian Patent Application No. 2,695,161, which claims priority to PCT/IB2007/004553 filed on Oct. 31, 2007 (Applicant—Ocean Nutrition Canada Ltd. // Inventors—Burja et al.) (2 pages).

Voluntary Amendment filed Jun. 11, 2010 for Canadian Patent Application No. 2,695,161, which claims priority to PCT/IB2007/004553 filed on Oct. 31, 2007 (Applicant—Ocean Nutrition Canada Ltd. // Inventors—Burja et al.) (4 pages).

Response to Second Office Action filed in Jul. 2012 for Chinese Patent Application No. 200780100540.5, which claims priority to PCT/IB2007/004553 filed on Oct. 31, 2007(Applicant—Ocean Nutrition Canada Ltd. // Inventors—Burja et al.) (9 pages).

Second Office Action mailed Feb. 23, 2012 for Chinese Patent Application No. 200780100540.5, which claims priority to PCT/IB2007/004553 filed on Oct. 31, 2007 (Applicant—Ocean Nutrition Canada Ltd. // Inventors—Burja et al.) (11 pages).

Response to First Office Action filed in Nov. 2011 for Chinese Patent Application No. 200780100540.5, which claims priority to PCT/IB2007/004553 filed on Oct. 31, 2007 (Applicant—Ocean Nutrition Canada Ltd. // Inventors—Burja et al.) (9 pages).

First Office Action mailed Jul. 5, 2011 for Chinese Patent Application No. 200780100540.5, which claims priority to PCT/IB2007/004553 filed on Oct. 31, 2007 (Applicant—Ocean Nutrition Canada Ltd. // Inventors—Burja et al.) (13 pages).

Response to Article 94(3) EPC Communication filed Mar. 29, 2012 for European Patent Application No. 07 872 485.3-1212, which claims priority to PCT/IB2007/004553 filed on Oct. 31, 2007 (Applicant—Ocean Nutrition Canada Ltd. // Inventors—Burja et al.) (9 pages).

Article 94(3) EPC Communication mailed Sep. 30, 2011 for European Patent Application No. 07 872 485.3-1212, which claims priority to PCT/IB2007/004553 filed on Oct. 31, 2007 (Applicant—Ocean Nutrition Canada Ltd. // Inventors—Burja et al.) (8 pages).

Response to Rules 70(2) and 70a(2) Communication filed Jun. 27, 2011 for European Patent Application No. 07 872 485.3-1212, which claims priority to PCT/IB2007/004553 filed on Oct. 31, 2007 (Applicant—Ocean Nutrition Canada Ltd. // Inventors—Burja et al.) (16 pages).

Rules 70(2) and 70a(2) Communication mailed Dec. 20, 2010 for European Patent Application No. 07 872 485.3-1212, which claims priority to PCT/IB2007/004553 filed on Oct. 31, 2007 (Applicant—Ocean Nutrition Canada Ltd. // Inventors—Burja et al.) (14 pages).

Extended European Search Report mailed Dec. 1, 2010 for European Patent Application No. 07 872 485.3-1212, which claims priority to PCT/IB2007/004553 filed on Oct. 31, 2007 (Applicant—Ocean Nutrition Canada Ltd. // Inventors—Burja et al.) (13 pages).

* cited by examiner

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: synthetic construct; forward primer

<400> SEQUENCE: 1
ggracagcga sttttacagg g                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic construct; reverse primer

<400> SEQUENCE: 2
gtgctcaatc tggtggttka g                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic construct; forward primer

<400> SEQUENCE: 3
aagccyttcg agctcaagty c                                              21

<210> SEQ ID NO 4
<211> LENGTH: 20
<212> TYPE: DNA
<213> ORGANISM: Artificial Sequence
<220> FEATURE:
<223> OTHER INFORMATION: synthetic construct; reverse primer

<400> SEQUENCE: 4
gcacgaaraa gttgccgaag                                                20
```

<210> SEQ ID NO 5
<211> LENGTH: 1003
<212> TYPE: DNA
<213> ORGANISM: Artificial Sequence
<220> FEATURE:
<223> OTHER INFORMATION: synthetic construct; 600-16 clone without
      vector sequence synthesized from recombinant plasmid

<400> SEQUENCE: 5

```
aagcctttcg agctcaagtc catcacgccg tcatgcgatc tccgccctcc gctgcttctt     60
ctcgagcttt ggcagagccg ccgcattgcg aactgccgcc atccatcgg tcgttgcagc    120 acccggtaag tctgctgacc aggagggct gggagcgaag agggcgtaca gcggagaggt     180
agcgctcaag ctcagacctc cagcgcccga agcaagattt tggtcattgg cccgggccct    240
gaccagattc tcgaggtctc ggactcgtct tctggtgact ctcatgagac tggattctcg    300
ccttcgccaa tgaactcgtc tgtagtcccc atatatcgat ccgtcgac atcgcatctc      360 ccggacctct cctccacccg cgacactctt gactcctcct tcggcaactt tttcgtgaag    420
cctttcgagc tcaagtccct gaagctcgtg cacaacatct ttctcaccgg tctgtccctg    480
tacatggcta gcgagtgcgc gcgccaggcc tacctcggcg gctacaagct ctttggcaac    540
ccgatggaga agggtgccga gtctcacgcc ctaggcatgg ctagcattat ctacgttttt    600
tacgtgagca gttcctcga gtttcttgac acggtcttca tgatcctcgg caagaagtgg     660
aagcagctca gctttcttca cgtctaccac cacgcgagca tcagcttcat ctggggcatt    720
atcgcccgtt ttgcgcccgg tggcgacgcg tacttttcca ccatcctcaa cagcagcgtg    780
catgtcgtgc tctacggcta ctacgcctcg accacgctcg gctacacctt catgcgcccg    840
ctgcgcccgt acattactac catccagctc acgcagttca tggccatggt cgtccagtcc    900
gtctatgact actacaaccc ttgcgactac ccgcagcccc tcgtcaagct actcttctgg    960
tacatgctca ccatgctcgg cctcttcggc aacttcttcg tgc                     1003
```

<210> SEQ ID NO 6
<211> LENGTH: 28
<212> TYPE: DNA
<213> ORGANISM: Artificial Sequence
<220> FEATURE:
<223> OTHER INFORMATION: synthetic construct; oligonucleotide

<400> SEQUENCE: 6

```
cgctgcgccc gtacattact accatcca                                        28
```

<210> SEQ ID NO 7
<211> LENGTH: 21
<212> TYPE: DNA
<213> ORGANISM: Artificial Sequence
<220> FEATURE:
<223> OTHER INFORMATION: synthetic construct; oligonucleotide

<400> SEQUENCE: 7

```
gtcgtccagt ccgtctatga c                                               21
```

<210> SEQ ID NO 8
<211> LENGTH: 358
<212> TYPE: DNA
<213> ORGANISM: Artificial Sequence
<220> FEATURE:
<223> OTHER INFORMATION: synthetic construct; 3'C2-1 clone synthesized
      from recombinant plasmid

<400> SEQUENCE: 8

| | |
|---|---|
| tactacaacc cttgcgacta cccgcagccc ctcgtcaagc tactcttctg gtacatgctc | 60 |
| accatgctcg gccttttcgg caacttcttc gtgcagcagt acctcaagcc caaggcgcct | 120 |
| aagaagcaaa agaccatctg agccgagtcc catcccaaaa tacgtcacgc aagtgcgtac | 180 |
| tagtgggagt gaggggctgc aagtactact tattggtcac cgggtaagac cgctagaccg | 240 |
| caacttgtct tgaagcatag attgttgatt ctgtcgctac gaattcgagt ggaccccgga | 300 |
| ggtaaacgac gcgtgttcaa gggcgaattc gtttaaacct gcaggactag tcccttta | 358 |

<210> SEQ ID NO 9
<211> LENGTH: 28
<212> TYPE: DNA
<213> ORGANISM: Artificial Sequence
<220> FEATURE:
<223> OTHER INFORMATION: synthetic construct; oligonucleotide

<400> SEQUENCE: 9

| | |
|---|---|
| ctcggcaccc ttctccatcg ggttgcca | 28 |

<210> SEQ ID NO 10
<211> LENGTH: 26
<212> TYPE: DNA
<213> ORGANISM: Artificial Sequence
<220> FEATURE:
<223> OTHER INFORMATION: synthetic construct; oligonucleotide

<400> SEQUENCE: 10

| | |
|---|---|
| gttgccaaag agcttgtagc cgccga | 26 |

<210> SEQ ID NO 11
<211> LENGTH: 519
<212> TYPE: DNA
<213> ORGANISM: Artificial Sequence
<220> FEATURE:
<223> OTHER INFORMATION: synthetic construct; 5' D2-11 clone synthesized
    from recombinant plasmid

<400> SEQUENCE: 11

| | |
|---|---|
| gagcttgtag ccgccgaggt aggcctggcg cgcgcactcg ctagccatgt acagggacag | 60 |
| accggtgaga aagatgttgt gcacgagctt caggaacttg agctcgaaag cttactcac | 120 |
| aaaggccgtc atgaaggcag acccgagaac cacgaacgcc aggtagccga cgatgagcgc | 180 |
| catcatctcc tcggtcgaga taaagagctt gccctcgttc agcttgttgg gcttttcgtg | 240 |
| ctccatgaat tccacgatcc ggttgtctac ggcgtccacg aaccggcgcc attgctgccc | 300 |
| ggcgacctcc atcgtgccta cgctgctggc gcgcctcttt cgctcgagct gctcgctagc | 360 |
| actaggccct gtgatctgcc cagtcctcgt gatagattcc ggttttgccg gctggccgtc | 420 |
| accaggcggt cccggccatc atcagccagg tttgtcaccc cgaggtaaac gacgcgtgtt | 480 |
| caagggcgaa ttcgtttaaa cctgcaggac tagtccctt | 519 |

<210> SEQ ID NO 12
<211> LENGTH: 19
<212> TYPE: DNA
<213> ORGANISM: Artificial Sequence
<220> FEATURE:
<223> OTHER INFORMATION: synthetic construct; forward primer

<400> SEQUENCE: 12

| | |
|---|---|
| gctgatgatg gccgggacc | 19 |

<210> SEQ ID NO 13

<211> LENGTH: 21
<212> TYPE: DNA
<213> ORGANISM: Artificial Sequence
<220> FEATURE:
<223> OTHER INFORMATION: synthetic construct; reverse primer

<400> SEQUENCE: 13
ggtccactcg aattcgtagc g                                                 21

<210> SEQ ID NO 14
<211> LENGTH: 1119
<212> TYPE: DNA
<213> ORGANISM: Artificial Sequence
<220> FEATURE:
<223> OTHER INFORMATION: synthetic construct; ONCT-18Elo clone
      synthesized from recombinant plasmid
<220> FEATURE:
<221> NAME/KEY: CDS
<222> LOCATION: (135)..(965)

<400> SEQUENCE: 14

```
gctgatgatg gccgggaccg cctggtgacg gccagccggc aaaaccggaa tctatcacga          60
ggactgggca gatcacaggg cctagtgcta gcgagcagct cgagcgaaag aggcgcgcca         120
gcagcgtagg cacg atg gag gtc gcc ggg cag caa tgg cgc cgg ttc gtg          170
              Met Glu Val Ala Gly Gln Gln Trp Arg Arg Phe Val
                1               5                  10 gac gcc gta gac aac cgg atc gtg gaa ttc atg gag cac gaa aag ccc          218
Asp Ala Val Asp Asn Arg Ile Val Glu Phe Met Glu His Glu Lys Pro
             15                  20                  25 aac aag ctg aac gag ggc aag ctc ttt atc tcg acc gag gag atg atg          266
Asn Lys Leu Asn Glu Gly Lys Leu Phe Ile Ser Thr Glu Glu Met Met
 30                  35                  40 gcg ctc atc gtc ggc tac ctg gcg ttc gtg gtt ctc ggg tct gcc ttc          314
Ala Leu Ile Val Gly Tyr Leu Ala Phe Val Val Leu Gly Ser Ala Phe
 45                  50                  55                  60 atg acg gcc ttt gtg agt aag cct ttc gag ctc aag ttc ctg aag ctc          362
Met Thr Ala Phe Val Ser Lys Pro Phe Glu Leu Lys Phe Leu Lys Leu
             65                  70                  75 gtg cac aac atc ttt ctc acc ggt ctg tcc ctg tac atg gct agc gag          410
Val His Asn Ile Phe Leu Thr Gly Leu Ser Leu Tyr Met Ala Ser Glu
             80                  85                  90 tgc gcg cgc cag gcc tac ctc ggc ggc tac aag ctc ttt ggc aac ccg          458
Cys Ala Arg Gln Ala Tyr Leu Gly Gly Tyr Lys Leu Phe Gly Asn Pro
             95                 100                 105 atg gag aag ggt gcc gag tct cac gcc cta ggc atg gct agc att atc          506
Met Glu Lys Gly Ala Glu Ser His Ala Leu Gly Met Ala Ser Ile Ile
110                 115                 120 tac gtt ttt tac gtg agc aag ttc ctc gag ttt ctt gac acg tcc ttc          554
Tyr Val Phe Tyr Val Ser Lys Phe Leu Glu Phe Leu Asp Thr Val Phe
125                 130                 135                 140 atg atc ctc ggc aag aag tgg aag cag ctc agc ttt ctt cac gtc tac          602
Met Ile Leu Gly Lys Lys Trp Lys Gln Leu Ser Phe Leu His Val Tyr
             145                 150                 155 cac cac gcg agc atc agc ttc atc tgg ggc att atc gcc cgt ttt gcg          650
His His Ala Ser Ile Ser Phe Ile Trp Gly Ile Ile Ala Arg Phe Ala
             160                 165                 170 ccc ggt ggc gac gcg tac ttt tcc acc atc ctc aac agc agc gtg cat          698
Pro Gly Gly Asp Ala Tyr Phe Ser Thr Ile Leu Asn Ser Ser Val His
             175                 180                 185 gtc gtg ctc tac ggc tac tac gcc tcg acc acg ctc ggc tac acc ttc          746
Val Val Leu Tyr Gly Tyr Tyr Ala Ser Thr Thr Leu Gly Tyr Thr Phe
             190                 195                 200
```

```
atg cgc ccg ctg cgc ccg tac att act acc atc cag ctc acg cag ttc    794
Met Arg Pro Leu Arg Pro Tyr Ile Thr Thr Ile Gln Leu Thr Gln Phe
205                 210                 215                 220 atg gcc atg gtc gtc cag tcc gtc tat gac tac tac aac cct tgc gac    842
Met Ala Met Val Val Gln Ser Val Tyr Asp Tyr Tyr Asn Pro Cys Asp
                225                 230                 235 tac ccg cag ccc ctc gtc aag cta ctc ttc tgg tac atg ctc acc atg    890
Tyr Pro Gln Pro Leu Val Lys Leu Leu Phe Trp Tyr Met Leu Thr Met
            240                 245                 250 ctc ggc ctc ttc ggc aac ttc ttc gtg cag cag tac ctc aag ccc aag    938
Leu Gly Leu Phe Gly Asn Phe Phe Val Gln Gln Tyr Leu Lys Pro Lys
        255                 260                 265 gcg cct aag aag caa aag acc atc tga gccgagtccc atcccaaaat          985
Ala Pro Lys Lys Gln Lys Thr Ile
    270                 275 acgtcacgca agtgcgtact agtgggagtg aggggctgca agtactactt attggtcacc  1045
gggtaagacc gctagaccgc aacttgtctt gaagcataga ttgttgattc tgtcgctacg  1105
aattcgagtg gacc                                                   1119

<210> SEQ ID NO 15
<211> LENGTH: 276
<212> TYPE: PRT
<213> ORGANISM: Artificial Sequence
<220> FEATURE:
<223> OTHER INFORMATION: Synthetic Construct

<400> SEQUENCE: 15

Met Glu Val Ala Gly Gln Gln Trp Arg Arg Phe Val Asp Ala Val Asp
1               5                   10                  15

Asn Arg Ile Val Glu Phe Met Glu His Glu Lys Pro Asn Lys Leu Asn
            20                  25                  30

Glu Gly Lys Leu Phe Ile Ser Thr Glu Glu Met Met Ala Leu Ile Val
        35                  40                  45

Gly Tyr Leu Ala Phe Val Val Leu Gly Ser Ala Phe Met Thr Ala Phe
    50                  55                  60

Val Ser Lys Pro Phe Glu Leu Lys Phe Lys Leu Val His Asn Ile
65                  70                  75                  80

Phe Leu Thr Gly Leu Ser Leu Tyr Met Ala Ser Glu Cys Ala Arg Gln
                85                  90                  95

Ala Tyr Leu Gly Gly Tyr Lys Leu Phe Gly Asn Pro Met Glu Lys Gly
            100                 105                 110

Ala Glu Ser His Ala Leu Gly Met Ala Ser Ile Ile Tyr Val Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220
```

Val Gln Ser Val Tyr Asp Tyr Tyr Asn Pro Cys Asp Tyr Pro Gln Pro
225                 230                 235                 240

Leu Val Lys Leu Leu Phe Trp Tyr Met Leu Thr Met Leu Gly Leu Phe
            245                 250                 255

Gly Asn Phe Phe Val Gln Gln Tyr Leu Lys Pro Lys Ala Pro Lys Lys
        260                 265                 270

Gln Lys Thr Ile
        275

<210> SEQ ID NO 16
<211> LENGTH: 276
<212> TYPE: PRT
<213> ORGANISM: Artificial Sequence
<220> FEATURE:
<223> OTHER INFORMATION: synthetic construct; ONCT18_d5elongase peptide

<400> SEQUENCE: 16

Met Glu Val Ala Gly Gln Gln Trp Arg Arg Phe Val Asp Ala Val Asp
1               5                   10                  15

Asn Arg Ile Val Glu Phe Met Glu His Glu Lys Pro Asn Lys Leu Asn
            20                  25                  30

Glu Gly Lys Leu Phe Ile Ser Thr Glu Glu Met Met Ala Leu Ile Val
        35                  40                  45

Gly Tyr Leu Ala Phe Val Val Leu Gly Ser Ala Phe Met Thr Ala Phe
    50                  55                  60

Val Ser Lys Pro Phe Glu Leu Lys Phe Leu Lys Leu Val His Asn Ile
65                  70                  75                  80

Phe Leu Thr Gly Leu Ser Leu Tyr Met Ala Ser Glu Cys Ala Arg Gln
                85                  90                  95

Ala Tyr Leu Gly Gly Tyr Lys Leu Phe Gly Asn Pro Met Glu Lys Gly
            100                 105                 110

Ala Glu Ser His Ala Leu Gly Met Ala Ser Ile Ile Tyr Val Phe Tyr
        115                 120                 125

Val Ser Lys Phe Leu Glu Phe Leu Asp Thr Val Phe Met Ile Leu Gly
    130                 135                 140

Lys Lys Trp Lys Gln Leu Ser Phe Leu His Val Tyr His His Ala Ser
145                 150                 155                 160

Ile Ser Phe Ile Trp Gly Ile Ile Ala Arg Phe Ala Pro Gly Gly Asp
                165                 170                 175

Ala Tyr Phe Ser Thr Ile Leu Asn Ser Ser Val His Val Val Leu Tyr
            180                 185                 190

Gly Tyr Tyr Ala Ser Thr Thr Leu Gly Tyr Thr Phe Met Arg Pro Leu
        195                 200                 205

Arg Pro Tyr Ile Thr Thr Ile Gln Leu Thr Gln Phe Met Ala Met Val
    210                 215                 220

Val Gln Ser Val Tyr Asp Tyr Tyr Asn Pro Cys Asp Tyr Pro Gln Pro
225                 230                 235                 240

Leu Val Lys Leu Leu Phe Trp Tyr Met Leu Thr Met Leu Gly Leu Phe
                245                 250                 255

Gly Asn Phe Phe Val Gln Gln Tyr Leu Lys Pro Lys Ala Pro Lys Lys
            260                 265                 270

Gln Lys Thr Ile
        275

<210> SEQ ID NO 17
<211> LENGTH: 967

```
<212> TYPE: DNA
<213> ORGANISM: Artificial Sequence
<220> FEATURE:
<223> OTHER INFORMATION: synthetic construct; 10-3 4DES clone
      synthesized from recombinant plasmid

<400> SEQUENCE: 17
tacagggtga tgcgcgagcg cgtcgtggcc cggctcaggg agcgcggcaa ggcccgccgc    60
ggtggctatg agctctggac taaggcattt ctgctcctcg tgggtttctg gagctcgttg   120
tactggatgt gcacgctgga cccctcgttc ggggccatct tggccgccat gtcgctgggc   180
gtctttgccg ccttcgtggg cacgtgtatc cagcacgacg gcaaccatgg cgcttttgcc   240
cagtcgcgat gggtcaacaa ggttgccggg tggacgcttg acatgattgg cgccagtggc   300
atgacgtggg agttccagca cgtcctgggc caccacccgt acacgaacct gattgaggag   360
gaaaatggcc tgcaaaaggt gagcggcaag aaaatggaca ccaaggtggc cgaccaggag   420
agcgacccgg atgtcttctc cacgtaccca atgatgcgct gcacccgtg gcacgaaaag    480 cgctggtacc accgtttcca acacatttac ggcccgttca tcttcggctt catgaccatc   540
aacaaggtag tcacgcagga cgtcgaggtg gtgctccaca gcggctctt ccagattgac    600 gccgagtgcc ggtacgcgag tccgatgtac gtggcgcggt tctggatcat gaaggcgctc   660
acggtgctct acatggtggg cctgccttgc tattcgcagg gcccgtggca cggcctcaag   720
ctgttcgcga tcgcgcactt ttcgtgcggc gaggtgctgg cgaccatgtt cattgtgaat   780
cacatcatcg agggtgtctc ttacgcttcc aaggacgcgg tcaagggcac gatggcgcct   840
ccgaagacga tgcacggcgt gacgcccatg aacaacacgc gcaaggaggc ggaggcgcag   900
gcgtccagtc tggcgctgta gtcaagtcag tccgctcgac gactgggccg ctgtcagtgc   960
cagactt                                                             967

<210> SEQ ID NO 18
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 18
ttacgcttcc aaggacgcgg tc                                             22

<210> SEQ ID NO 19
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 19
atgaacaaca cgcgcaagga gg                                             22

<210> SEQ ID NO 20
<211> LENGTH: 782
<212> TYPE: DNA
<213> ORGANISM: Artificial Sequence
<220> FEATURE:
<223> OTHER INFORMATION: synthetic construct; 3' D2-92 clone synthesized
      from recombinant plasmid

<400> SEQUENCE: 20
atgaacaaca cgcgcaagga ggcggaggcg caggcgtcca gtccggcgc tgtagtcaag     60
```

```
tcagtcccgc tcgacgactg ggccgctgtc cagtgccaga cttcggtgaa ttggagcgtc    120
ggctcatggt tctggaacca cttttccggc ggcctcaacc accagatcga gcaccatctg    180
ttccctgggc tcagccacga gacgtactac cacattcagg acgtcgttca gtctacctgc    240
gccgagtacg gagtcccgta ccagcacgaa ccctcgctct ggactgcgta ctggaagatg    300
ctcgagcacc tccgtcagct tggcaatgag gagacccacg agtcctggca gcacactgcc    360
tgatgggctg acgagggcgg gtgcgaccaa tttacagttc cttgatcacg agaggctcca    420
caaccagagc acagcagtgc tgcgccggcg tcaatgttcc gtcaattggg tgaaacgcct    480
ccgggtgcgc ggctgggctc ttgtttgatt gcttgcttgc ttgcatgcga gcttgttaca    540
agaccgagcc acccacagcc cgtccatgca tctggggaac agcttgaagt atgaagtact    600
acgtacccgt ttaagcttta aaaaaaggtc aagtcttatc atgaatgcta atgacgattc    660
gctggcgctc atcagaggca accaatcctc agcaaaaggt ttgcaaaggc caaaagaag    720 tcagcgctag cgccacatgc ataaatcagg gctgtcaccc cggaggtaaa cgacgcgtgt    780
tc                                                                  782

<210> SEQ ID NO 21
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 21
ctggatacac gtgcccacga ag                                            22

<210> SEQ ID NO 22
<211> LENGTH: 26
<212> TYPE: DNA
<213> ORGANISM: Artificial Sequence
<220> FEATURE:
<223> OTHER INFORMATION: synthetic construct; primer

<400> SEQUENCE: 22
cacatccagt acaacgagct ccagaa                                        26

<210> SEQ ID NO 23
<211> LENGTH: 946
<212> TYPE: DNA
<213> ORGANISM: Artificial Sequence
<220> FEATURE:
<223> OTHER INFORMATION: synthetic construct; 5'-217 clone synthesized
      from recombinant plasmid

<400> SEQUENCE: 23
cacatccagt acaacgagct ccagaaaccc acgaggagca gaaatgcctt agtccagagc    60
tcatagccac cgcggcgggc cttgccgcgc tccctgagcc gggccacgac gcgctcgcgc    120
atcactttgt aaaagtcgct gttccacgtg tagtacgagg ccgacgggag gcctgaaagc    180
gtccgctttt ccttctcatt tgcgccgcct tggccatccg gcagcttccc gatccggtac    240
ttgcgcagca ccgcgtccga gacgccccgc acatggtacg tctcatacaa cacggtggcc    300
tccttgcctg cggccagaag gattatgtcg ccgcccgggt gcacgctcgc gaacttggtt    360
acatcgtaca cgagcccgtg gatcgcgcac caggcgtcat ccggcttgtt gtgcgcgcgg    420
acctgctcga acgagatctc ctcgtcgtag ccgactgtca tcctgacccc tgcgggcagt    480
cctgcctact tcgatcaaat tccttcgcct acggtcgcgc gctccagcgt cagttccccc    540
```

```
tgctcagtga aaggctccaa agcttgcggt tctcaatcgc acccagcgcg tccagcctgg      600
gttttgcgcg ctccggcaag atttactgcc aaggatgacg tcatgcgttt cgttcgttcg      660
tccaagtagt ggcccgatcc ccggcccaag cgcccagctt tgcttgcgag cgaagctccg      720
cgcccgtaca cacgcgctcc tggctgctag cgccatcgcg tggcggggca tcgaccgcat      780
gacgttggcg tcgatcatga agacgtgcgt acgtacgtac ctaatggtct acctcgacgg      840
cgatgttcgg gctttgcagc aggatgctca ccccggaggt aaacgacgcg tgttcatctg      900
aattcgtcga caagcttctc gagcctaggc tagctctaga ccacac                    946
```

```
<210> SEQ ID NO 24
<211> LENGTH: 21
<212> TYPE: DNA
<213> ORGANISM: Artificial Sequence
<220> FEATURE:
<223> OTHER INFORMATION: synthetic construct; ONC-T184des380F primer

<400> SEQUENCE: 24
cgattgagaa ccgcaagctt t                                                 21

<210> SEQ ID NO 25
<211> LENGTH: 21
<212> TYPE: DNA
<213> ORGANISM: Artificial Sequence
<220> FEATURE:
<223> OTHER INFORMATION: synthetic construct; ONC-T184des1687R primer

<400> SEQUENCE: 25
gcagcactgc tgtgctctgg t                                                 21

<210> SEQ ID NO 26
<211> LENGTH: 1758
<212> TYPE: DNA
<213> ORGANISM: Artificial Sequence
<220> FEATURE:
<223> OTHER INFORMATION: synthetic construct; complete Phusion PCR
      T18_d4desat clone synthesized from recombinant plasmid
<220> FEATURE:
<221> NAME/KEY: CDS
<222> LOCATION: (119)..(1678)

<400> SEQUENCE: 26
cgattgagaa ccgcaagctt tggagccttt cactgagcag ggggaactga cgctggagcg       60
cgcgaccgta ggcgaaggaa tttgatcgaa gtaggcagga ctgcctgcag gggtcaag        118
```

```
atg aca gtc ggc tac gac gag gag atc tcg ttc gag cag gtc cgc gcg        166
Met Thr Val Gly Tyr Asp Glu Glu Ile Ser Phe Glu Gln Val Arg Ala
1               5                   10                  15 cac aac aag ccg gat gac gcc tgg tgc gcg atc cac ggg ctc gtg tac        214
His Asn Lys Pro Asp Asp Ala Trp Cys Ala Ile His Gly Leu Val Tyr
            20                  25                  30 gat gta acc aag ttc gcg agc gtg cac ccg ggc ggc gac ata atc ctt        262
Asp Val Thr Lys Phe Ala Ser Val His Pro Gly Gly Asp Ile Ile Leu
        35                  40                  45 ctg gcc gca ggc aag gag gcc acc gtg ttg tat gag acg tac cat gtg        310
Leu Ala Ala Gly Lys Glu Ala Thr Val Leu Tyr Glu Thr Tyr His Val
    50                  55                  60 cgg ggc gtc tcg gac gcg gtg ctg cgc aag tac cgg atc ggg aag ctg        358
Arg Gly Val Ser Asp Ala Val Leu Arg Lys Tyr Arg Ile Gly Lys Leu
65                  70                  75                  80 ccg gat ggc caa ggc ggc gca aat gag aag gaa aag cgg acg ctt tca        406
Pro Asp Gly Gln Gly Gly Ala Asn Glu Lys Glu Lys Arg Thr Leu Ser
                85                  90                  95
```

| | | | | | | | | | | | | | | | | |
|---|---|---|---|---|---|---|---|---|---|---|---|---|---|---|---|---|
| ggc | ctc | tcg | tcg | gcc | tcg | tac | tac | acg | tgg | aac | agc | gac | ttt | tac | aaa | 454 |
| Gly | Leu | Ser | Ser | Ala | Ser | Tyr | Tyr | Thr | Trp | Asn | Ser | Asp | Phe | Tyr | Lys | |
| | | 100 | | | | | 105 | | | | | 110 | | | | |
| gtg | atg | cgc | gag | cgc | gtc | gtg | gcc | cgg | ctc | agg | gag | cgc | ggc | aag | gcc | 502 |
| Val | Met | Arg | Glu | Arg | Val | Val | Ala | Arg | Leu | Arg | Glu | Arg | Gly | Lys | Ala | |
| | 115 | | | | | 120 | | | | | 125 | | | | | |
| cgc | cgc | ggt | ggc | tat | gag | ctc | tgg | act | aag | gca | ttt | ctg | ctc | ctc | gtg | 550 |
| Arg | Arg | Gly | Gly | Tyr | Glu | Leu | Trp | Thr | Lys | Ala | Phe | Leu | Leu | Leu | Val | |
| 130 | | | | | 135 | | | | | 140 | | | | | | |
| ggt | ttc | tgg | agc | tcg | ttg | tac | tgg | atg | tgc | acg | ctg | gac | ccc | tcg | ttc | 598 |
| Gly | Phe | Trp | Ser | Ser | Leu | Tyr | Trp | Met | Cys | Thr | Leu | Asp | Pro | Ser | Phe | |
| 145 | | | | 150 | | | | | 155 | | | | | 160 | | |
| ggg | gcc | atc | ttg | gcc | gcc | atg | tcg | ctg | ggc | gtc | ttt | gcc | gcc | ttt | gtg | 646 |
| Gly | Ala | Ile | Leu | Ala | Ala | Met | Ser | Leu | Gly | Val | Phe | Ala | Ala | Phe | Val | |
| | | | 165 | | | | | 170 | | | | | 175 | | | |
| ggc | acg | tgt | atc | cag | cac | gac | ggc | aac | cat | ggc | gct | ttt | gcc | cag | tcg | 694 |
| Gly | Thr | Cys | Ile | Gln | His | Asp | Gly | Asn | His | Gly | Ala | Phe | Ala | Gln | Ser | |
| | | | 180 | | | | | 185 | | | | | 190 | | | |
| cga | tgg | gtc | aac | aag | gtt | gcc | ggg | tgg | acg | ctt | gac | atg | att | ggc | gcc | 742 |
| Arg | Trp | Val | Asn | Lys | Val | Ala | Gly | Trp | Thr | Leu | Asp | Met | Ile | Gly | Ala | |
| | | 195 | | | | | 200 | | | | | 205 | | | | |
| agt | ggc | atg | acg | tgg | gag | ttc | cag | cac | gtc | ctg | ggc | cac | cac | ccg | tac | 790 |
| Ser | Gly | Met | Thr | Trp | Glu | Phe | Gln | His | Val | Leu | Gly | His | His | Pro | Tyr | |
| | 210 | | | | | 215 | | | | | 220 | | | | | |
| acg | aac | ctg | att | gag | gag | gaa | aat | ggc | ctg | caa | aag | gtg | agc | ggc | aag | 838 |
| Thr | Asn | Leu | Ile | Glu | Glu | Glu | Asn | Gly | Leu | Gln | Lys | Val | Ser | Gly | Lys | |
| 225 | | | | | 230 | | | | | 235 | | | | | 240 | |
| aaa | atg | gac | acc | aag | gtg | gcc | gac | cag | gag | agc | gac | ccg | gat | gtc | ttc | 886 |
| Lys | Met | Asp | Thr | Lys | Val | Ala | Asp | Gln | Glu | Ser | Asp | Pro | Asp | Val | Phe | |
| | | | 245 | | | | | 250 | | | | | 255 | | | |
| tcc | acg | tac | cca | atg | atg | cgc | ttg | cac | ccg | tgg | cac | gaa | aag | cgc | tgg | 934 |
| Ser | Thr | Tyr | Pro | Met | Met | Arg | Leu | His | Pro | Trp | His | Glu | Lys | Arg | Trp | |
| | | | 260 | | | | | 265 | | | | | 270 | | | |
| tac | cac | cgt | ttc | caa | cac | att | tac | ggc | ccg | ttc | atc | ttc | ggc | ttc | atg | 982 |
| Tyr | His | Arg | Phe | Gln | His | Ile | Tyr | Gly | Pro | Phe | Ile | Phe | Gly | Phe | Met | |
| | | 275 | | | | | 280 | | | | | 285 | | | | |
| acc | atc | aac | aag | gta | gtc | acg | cag | gac | gtc | gag | gtg | gtg | ctc | cac | aag | 1030 |
| Thr | Ile | Asn | Lys | Val | Val | Thr | Gln | Asp | Val | Glu | Val | Val | Leu | His | Lys | |
| | | 290 | | | | | 295 | | | | | 300 | | | | |
| cgg | ctc | ttc | cag | att | gac | gcc | gag | tgc | cgg | tac | gcg | agt | ccg | atg | tac | 1078 |
| Arg | Leu | Phe | Gln | Ile | Asp | Ala | Glu | Cys | Arg | Tyr | Ala | Ser | Pro | Met | Tyr | |
| 305 | | | | | 310 | | | | | 315 | | | | | 320 | |
| gtg | gcg | cgg | ttc | tgg | atc | atg | aag | gcg | ctc | acg | gtg | ctc | tac | atg | gtg | 1126 |
| Val | Ala | Arg | Phe | Trp | Ile | Met | Lys | Ala | Leu | Thr | Val | Leu | Tyr | Met | Val | |
| | | | | 325 | | | | | 330 | | | | | 335 | | |
| ggc | ctg | cct | tgc | tat | tcg | cag | ggc | ccg | tgg | cac | ggc | ctc | aag | ctg | ttc | 1174 |
| Gly | Leu | Pro | Cys | Tyr | Ser | Gln | Gly | Pro | Trp | His | Gly | Leu | Lys | Leu | Phe | |
| | | | 340 | | | | | 345 | | | | | 350 | | | |
| gcg | atc | gcg | cac | ttt | tcg | tgc | ggc | gag | gtg | ctg | gcg | acc | atg | ttc | att | 1222 |
| Ala | Ile | Ala | His | Phe | Ser | Cys | Gly | Glu | Val | Leu | Ala | Thr | Met | Phe | Ile | |
| | | | 355 | | | | | 360 | | | | | 365 | | | |
| gtg | aat | cac | atc | atc | gag | ggt | gtc | tct | tac | gct | tcc | aag | gac | gcg | gtc | 1270 |
| Val | Asn | His | Ile | Ile | Glu | Gly | Val | Ser | Tyr | Ala | Ser | Lys | Asp | Ala | Val | |
| | | 370 | | | | | 375 | | | | | 380 | | | | |
| aag | ggc | acg | atg | gcg | cct | ccg | aag | acg | atg | cac | ggc | gtg | acg | ccc | atg | 1318 |
| Lys | Gly | Thr | Met | Ala | Pro | Pro | Lys | Thr | Met | His | Gly | Val | Thr | Pro | Met | |
| 385 | | | | | 390 | | | | | 395 | | | | | 400 | |
| aac | aac | acg | cgc | aag | gag | gcg | gag | gcg | cag | gcg | tcc | aag | tct | ggc | gct | 1366 |
| Asn | Asn | Thr | Arg | Lys | Glu | Ala | Glu | Ala | Gln | Ala | Ser | Lys | Ser | Gly | Ala | |

```
                    405                 410                 415
gta gtc aag tca gtc ccg ctc gac gac tgg gcc gct gtc cag tgc cag    1414
Val Val Lys Ser Val Pro Leu Asp Asp Trp Ala Ala Val Gln Cys Gln
            420                 425                 430 act tcg gtg aat tgg agc gtc ggc tca tgg ttc tgg aac cac ttt tcc    1462
Thr Ser Val Asn Trp Ser Val Gly Ser Trp Phe Trp Asn His Phe Ser
        435                 440                 445 ggc ggc ctc aac cac cag atc gag cac cat ctg ttc cct ggg ctc agc    1510
Gly Gly Leu Asn His Gln Ile Glu His His Leu Phe Pro Gly Leu Ser
    450                 455                 460 cac gag acg tac tac cac att cag gac gtc gtt cag tct acc tgc gcc    1558
His Glu Thr Tyr Tyr His Ile Gln Asp Val Val Gln Ser Thr Cys Ala
465                 470                 475                 480 gag tac gga gtc ccg tac cag cac gaa ccc tcg ctc tgg act gcg tac    1606
Glu Tyr Gly Val Pro Tyr Gln His Glu Pro Ser Leu Trp Thr Ala Tyr
                485                 490                 495 tgg aag atg ctc gag cac ctc cgt cag ctt ggc aat gag gag acc cac    1654
Trp Lys Met Leu Glu His Leu Arg Gln Leu Gly Asn Glu Glu Thr His
            500                 505                 510 gag tcc tgg cag cac act gcc tga tgggctgaca agggcgggtg cgaccaattt   1708
Glu Ser Trp Gln His Thr Ala
        515 acagttcctt gatcacgaga ggctccacaa ccagagcaca gcagtgctgc             1758

<210> SEQ ID NO 27
<211> LENGTH: 519
<212> TYPE: PRT
<213> ORGANISM: Artificial Sequence
<220> FEATURE:
<223> OTHER INFORMATION: Synthetic Construct

<400> SEQUENCE: 27

Met Thr Val Gly Tyr Asp Glu Glu Ile Ser Phe Glu Gln Val Arg Ala
1               5                   10                  15

His Asn Lys Pro Asp Asp Ala Trp Cys Ala Ile His Gly Leu Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Lys
            100                 105                 110

Val Met Arg Glu Arg Val Val Ala Arg Leu Arg Glu Arg Gly Lys Ala
        115                 120                 125

Arg Arg Gly Gly Tyr Glu Leu Trp Thr Lys Ala Phe Leu Leu Leu Val
    130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
```

```
              195                 200                 205
Ser Gly Met Thr Trp Glu Phe Gln His Val Leu Gly His Pro Tyr
210                 215                 220

Thr Asn Leu Ile Glu Glu Asn Gly Leu Gln Lys Val Ser Gly Lys
225                 230                 235                 240

Lys Met Asp Thr Lys Val Ala Asp Gln Glu Ser Asp Pro Asp Val Phe
                245                 250                 255

Ser Thr Tyr Pro Met Met Arg Leu His Pro Trp His Glu Lys Arg Trp
                260                 265                 270

Tyr His Arg Phe Gln His Ile Tyr Gly Pro Ile Phe Gly Phe Met
                275                 280                 285

Thr Ile Asn Lys Val Val Thr Gln Asp Val Glu Val Val Leu His Lys
                290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Gly Leu Pro Cys Tyr Ser Gln Gly Pro Trp His Gly Leu Lys Leu Phe
                340                 345                 350

Ala Ile Ala His Phe Ser Cys Gly Glu Val Leu Ala Thr Met Phe Ile
                355                 360                 365

Val Asn His Ile Ile Glu Gly Val Ser Tyr Ala Ser Lys Asp Ala Val
                370                 375                 380

Lys Gly Thr Met Ala Pro Pro Lys Thr Met His Gly Val Thr Pro Met
385                 390                 395                 400

Asn Asn Thr Arg Lys Glu Ala Glu Ala Gln Ala Ser Lys Ser Gly Ala
                405                 410                 415

Val Val Lys Ser Val Pro Leu Asp Asp Trp Ala Ala Val Gln Cys Gln
                420                 425                 430

Thr Ser Val Asn Trp Ser Val Gly Ser Trp Phe Trp Asn His Phe Ser
                435                 440                 445

Gly Gly Leu Asn His Gln Ile Glu His His Leu Phe Pro Gly Leu Ser
                450                 455                 460

His Glu Thr Tyr Tyr His Ile Gln Asp Val Val Gln Ser Thr Cys Ala
465                 470                 475                 480

Glu Tyr Gly Val Pro Tyr Gln His Gly Pro Ser Leu Trp Thr Ala Tyr
                485                 490                 495

Trp Lys Met Leu Glu His Leu Arg Gln Leu Gly Asn Glu Glu Thr His
                500                 505                 510

Glu Ser Trp Gln His Thr Ala
        515

<210> SEQ ID NO 28
<211> LENGTH: 519
<212> TYPE: PRT
<213> ORGANISM: Artificial Sequence
<220> FEATURE:
<223> OTHER INFORMATION: synthetic construct; T18_d4desat peptide

<400> SEQUENCE: 28

Met Thr Val Gly Tyr Asp Glu Glu Ile Ser Phe Glu Gln Val Arg Ala
1               5                   10                  15
```

-continued

```
His Asn Lys Pro Asp Asp Ala Trp Cys Ala Ile His Gly Leu Val Tyr
             20                  25                  30

Asp Val Thr Lys Phe Ala Ser Val His Pro Gly Gly Asp Ile Ile Leu
         35                  40                  45

Leu Ala Ala Gly Lys Glu Ala Thr Val Leu Tyr Glu Thr Tyr His Val
 50                  55                  60

Arg Gly Val Ser Asp Ala Val Leu Arg Lys Tyr Arg Ile Gly Lys Leu
 65                  70                  75                  80

Pro Asp Gly Gln Gly Gly Ala Asn Glu Lys Lys Arg Thr Leu Ser
                 85                  90                  95

Gly Leu Ser Ser Ala Ser Tyr Tyr Thr Trp Asn Ser Asp Phe Tyr Lys
                100                 105                 110

Val Met Arg Glu Arg Val Val Ala Arg Leu Arg Glu Arg Gly Lys Ala
            115                 120                 125

Arg Arg Gly Gly Tyr Glu Leu Trp Thr Lys Ala Phe Leu Leu Leu Val
130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
                180                 185                 190

Arg Trp Val Asn Lys Val Ala Gly Trp Thr Leu Asp Met Ile Gly Ala
            195                 200                 205

Ser Gly Met Thr Trp Glu Phe Gln His Val Leu Gly His His Pro Tyr
210                 215                 220

Thr Asn Leu Ile Glu Glu Glu Asn Gly Leu Gln Lys Val Ser Gly Lys
225                 230                 235                 240

Lys Met Asp Thr Lys Val Ala Asp Gln Glu Ser Asp Pro Asp Val Phe
                245                 250                 255

Ser Thr Tyr Pro Met Met Arg Leu His Pro Trp His Glu Lys Arg Trp
                260                 265                 270

Tyr His Arg Phe Gln His Ile Tyr Gly Pro Phe Ile Phe Gly Phe Met
            275                 280                 285

Thr Ile Asn Lys Val Val Thr Gln Asp Val Glu Val Val Leu His Lys
290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Gly Leu Pro Cys Tyr Ser Gln Gly Pro Trp His Gly Leu Lys Leu Phe
                340                 345                 350

Ala Ile Ala His Phe Ser Cys Gly Glu Val Leu Ala Thr Met Phe Ile
            355                 360                 365

Val Asn His Ile Ile Glu Gly Val Ser Tyr Ala Ser Lys Asp Ala Val
            370                 375                 380

Lys Gly Thr Met Ala Pro Pro Lys Thr Met His Gly Val Thr Pro Met
385                 390                 395                 400

Asn Asn Thr Arg Lys Glu Ala Glu Ala Gln Ala Ser Lys Ser Gly Ala
                405                 410                 415

Val Val Lys Ser Val Pro Leu Asp Asp Trp Ala Ala Val Gln Cys Gln
                420                 425                 430

Thr Ser Val Asn Trp Ser Val Gly Ser Trp Phe Trp Asn His Phe Ser
```

```
                        435                 440                 445
Gly Gly Leu Asn His Gln Ile Glu His His Leu Phe Pro Gly Leu Ser
        450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln His Thr Ala
            515

<210> SEQ ID NO 29
<211> LENGTH: 5
<212> TYPE: PRT
<213> ORGANISM: Artificial Sequence
<220> FEATURE:
<223> OTHER INFORMATION: synthetic construct; histidine_box1 peptide
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid

<400> SEQUENCE: 29

His Xaa Xaa His His
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic construct; histidine_box2 peptide
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid

<400> SEQUENCE: 30

Gln Xaa Xaa His His
1               5
```

D4 DESATURASES AND D5 ELONGASES

CROSS REFERENCE TO RELATED APPLICATIONS

The present application is a National Phase Application of International Application No. PCT/IB2007/004553, filed Oct. 31, 2007, which claims priority to U.S. Provisional Patent Application No. 60/949,730, filed on Jul. 13, 2007, which applications are incorporated herein fully by this reference.

REFERENCE TO SEQUENCE LISTING

The Sequence Listing submitted Jan. 22, 2014 as a text file named "15113_0032U2 Revised Sequence Listing," created on Jan. 22, 2014, and having a size of 38,501 bytes is hereby incorporated by reference pursuant to 37 C.F.R. §1.52(e)(5).

I. BACKGROUND

There is overwhelming scientific evidence that (n-3) highly unsaturated fatty acids such as docosahexaenoic acid (DHA) have a positive effect on cardio-circulatory diseases, chronic inflammations and brain disorders. The (n-6) fatty acids such as eicosapentaenoic acid (EPA) on the other hand have been noted as intermediate metabolites within the eicosanoid steroids, such as prostaglandins, leucotrienes or the like.

Currently, the main source of these highly unsaturated fatty acids is fish, with EPA and DHA noted within various blue fish (such as sardines and tuna) at amounts around 20% and 10%, respectively. It is believed that such a fatty acid profile occurs through the natural selection of optimal ratios for optimal performance within each species of fish. Yet, if one intends to use fish oil as the sole source of these lipids, several disadvantages exist, such as problems with flavor taint, uncontrollable fluctuations in availability and natural fish oil content variability. In addition, if one intends to obtain a highly purified (n-3) or (n-6) oil from these sources, it is very difficult to preferentially separate and purify.

Previously disclosed is a Thraustochytriales eukaryote, ONC-T18 and related organisms, capable of producing high amounts of DHA and EPA as well as other preferred fatty acids. ONC-T18 is disclosed in International Application PCT/IB2006/003977 and U.S. provisional applications 60/751,401 and 60/821,084 which are all herein incorporated by reference for information at least related to ONC-T18 and fatty acids produced therein. The manipulation of the DHA and EPA pathways is desirable. Disclosed herein is the isolation and characterization of two enzymes from ONC-T18 involved in these pathways, a D4 desaturase and a D5 elongase.

II. SUMMARY

Disclosed are methods and compositions related to ONC-T18, D4-desaturases, D5 elongases, their isolation, characterization, production, identification, and use for fatty acid production, as well as organisms containing these compositions and organisms expressing them.

III. BRIEF DESCRIPTION OF THE DRAWINGS

The accompanying drawings, which are incorporated in and constitute a part of this specification, illustrate several embodiments and together with the description illustrate the disclosed compositions and methods.

IV. DETAILED DESCRIPTION

Figure 1:
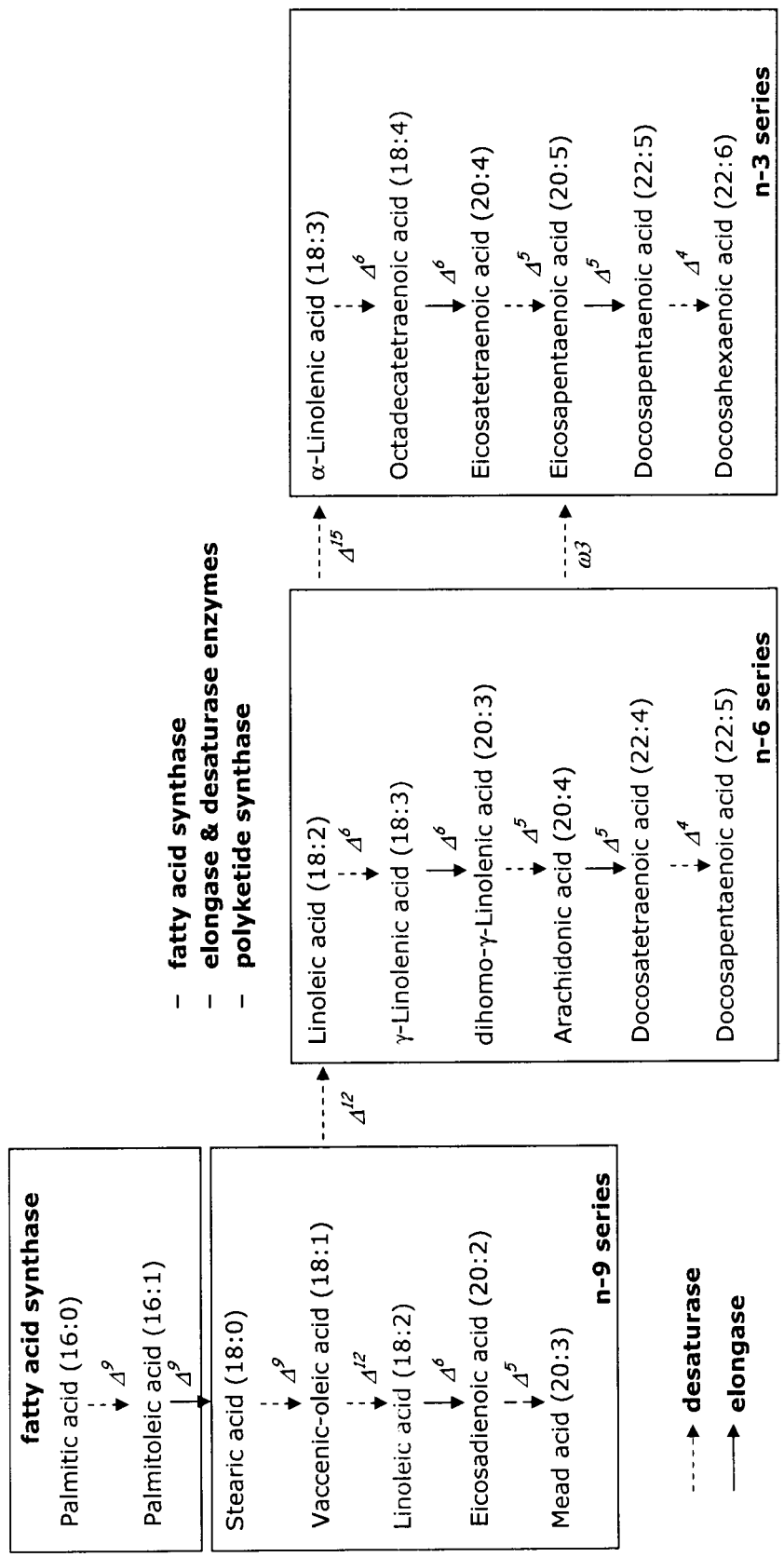
FIG. 1 shows the pathways of EPA and DHA production.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular D4 desaturase and D5 elongase is disclosed and discussed and a number of modifications that can be made to a number of molecules including the D4 desaturase and D5 elongase are discussed, specifically contemplated is each and every combination and permutation of D4 desaturase and D5 elongase and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. COMPOSITIONS

The use of omega-3 concentrates (eicosapentaenoic acid EPA, 20:5 n-3 and docosahexaenoic acid DHA, 22:6 n-3) has become important in the fortification of certain foods to promote a healthy diet. Thraustochytrids are marine protists that naturally produce DHA, at up to 20% of their biomass. The capability to ferment these organisms provides for a renewable, long-term source of these omega-3 oils. Characterisation of the fatty acid metabolic pathway (FIG. 1) reveals the importance of a D5-elongase responsible for the elongation of EPA into docosapentaenoic acid (DPA, 22:5 n-3), as well as a D4-desaturase being involved in the desaturation of DPA into DHA. Manipulation of the specific enzyme activity can influence the yield of EPA and DHA produced by our ONC-T18 strain as required by the needs of the market, and our customers.

Using degenerate primers constructed from a conserved region in the gene sequence from enzymes of different Thraustochytrid strains (*Thraustochytrium* sp. (CS020087), *Thraustochytrium aureum* (AF391546), *Thraustochytrium* sp. ATCC 34304 (AF391543), *Thraustochytrium* sp. ATCC 21685 (AF489589), and *Thraustochytrium* sp. FJN-10 (DQ133575) for D4-desaturase; *Thraustochytrium* sp. (CS160897) and Thraustochytrium aureum (CS160879) for D5-elongase) a D4-desaturase and a D5 elongase from ONC T-18 were isolated. Further a portion of the genes from genomic DNA (967 by and 593 bp, respectively) was PCR amplified. Genome walking APAGENE® GOLD kit, BIO S&T, Montreal, Quebec) was used to extend the known sequence to incorporate the entire open reading frame, and extend further to identify the adjacent genes on either side along with the promoter region. Primers were then constructed for the complete sequence to produce a full gene PCR product incorporating the entire open reading frame (1758 by and 1099 bp, respectively). The PCR product was cloned into pT7-Blue3 vector (Novagen, San Diego, Calif.) and transformed into *Escherichia coli* NovaBlue (DE3) (Novagen, San Diego, Calif.) and then sequenced.

Resultant gene plasmids were purified using the ULTRACLEAN® 6 Minute Mini Plasmid Prep kit (MO BIO Laboratories, Inc., Solana Beach, Calif.). The gene inserts were then excised using the restriction enzymes BamHI and NotI and cloned into the pYES2 yeast expression vector (Invitrogen, Carlsbad, Calif.). The new vector constructs identified as pYDes (D4-desaturase) and pYElo (D5-elongase) were then transformed into *Saccharomyces cerevisiae* INVSc1 using the S.c. EasyComp Transformation kit (Invitrogen, Carlsbad, Calif.), under the galactose promoter Gall. The negative control strain was INVSc1 containing the unaltered pYES2 vector, and these were grown simultaneously. The vector selection was done using the uracil auxotrophy of the yeast strain, SC medium without uracil was used.

The activity and specificity of the D4-desaturase and D5 elongase were determined using the yeast expression system. The transformed yeast was grown in SC-U medium containing 2% glucose, 1% Tergitol NP-40 for 48 hrs, 150 RPM at 30° C. A substrate medium was prepared containing SC-U, 2% galactose, 1% raffinose, 1% Tergitol NP-40 and 500 µM specific free fatty acid. The transformed yeast culture was inoculated into 100 ml substrate medium at an OD600 of 0.5 and cultures incubated at 20° C. for 5 days. The biomass was recovered by centrifugation at 2000 RPM for 5 min, washed once with 100 mM phosphate buffer (pH 7.0), then freeze dried. Fatty acid methyl ester gas chromatography was subsequently carried out to determine the efficiency of fatty acid desaturation and elongation. The percent conversion of the substrate was determined by calculating (product)/(substrate+product)*100.

Figures 2A, 2B:
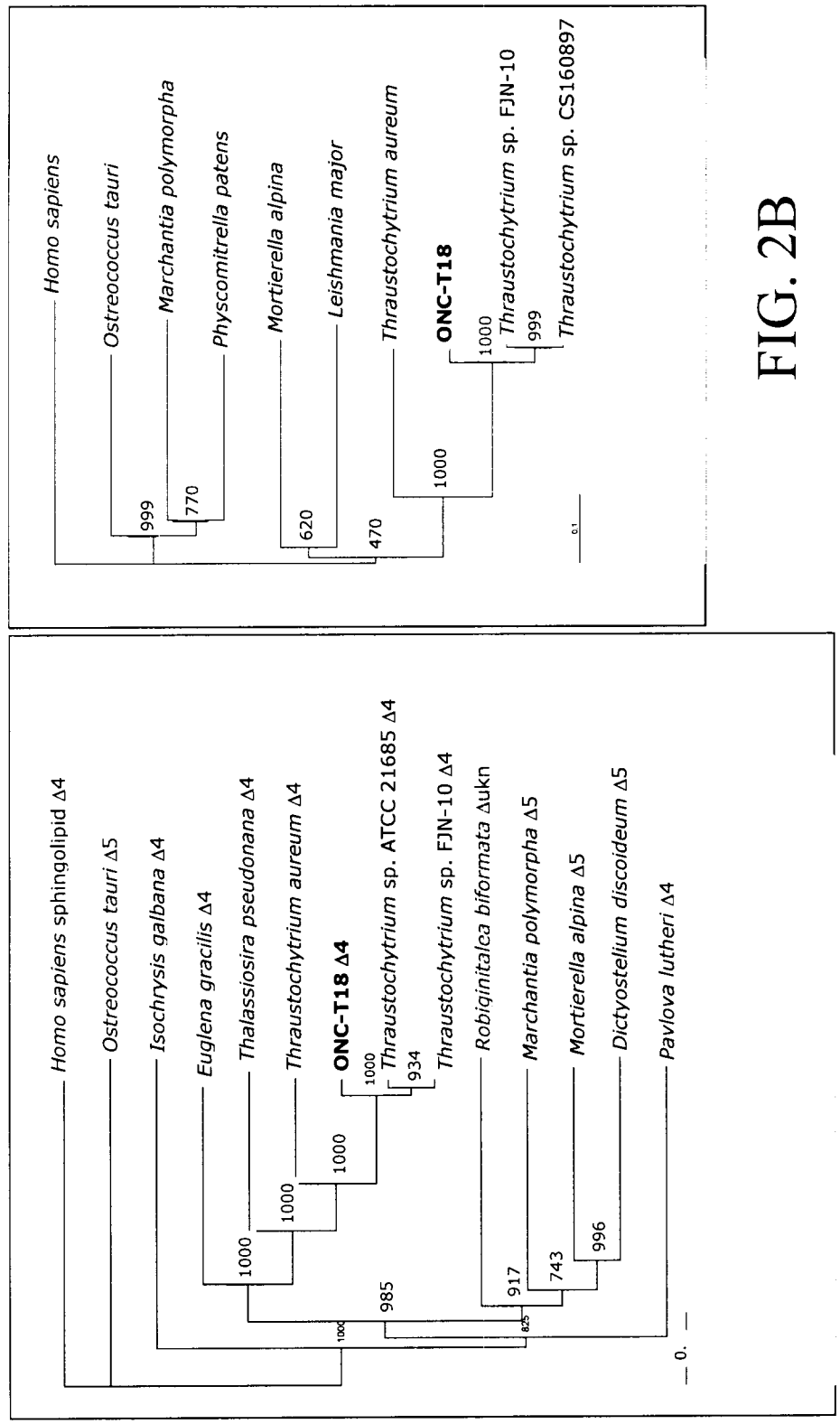
FIG. 2A shows a phylogentic tree for the isolated D4 desaturase and FIG. 2B shows a phlogenetic tree for the isolated D5-elongase.
Figure 3:
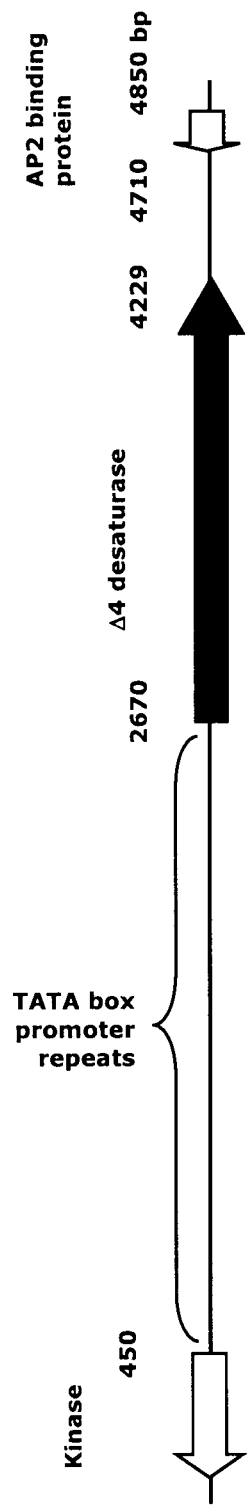
FIG. 3 shows a genetic outline schematic for the isolated D4 desaturase.

BLASTX™ results showed the ONC T-18 D4 desaturase to be 96% similar to a *Thraustochytrium* sp. ATCC 21685 D4-desaturase. FIG. 2A shows a rooted neighbour joining phylogenetic tree, determined using CLUSTALX™, bootstrap analysis (1000×) using the results of a BLASTX™ search when compared to the ONC-T18 D4-desaturase sequence. The D4-desaturase gene has an open reading frame of 1560 bp, transcribing a 519 amino acid protein. Analysis of this protein shows a cytochrome b5 domain with three histidine box motifs and four transmembrane regions, all elements characteristic of front-end desaturase. Adjacent to this gene are five putative TATA boxes, multiple repeat regions, two promoters and a protein kinase identified upstream and an AP2 binding protein downstream (FIG. 3).

Figure 4:
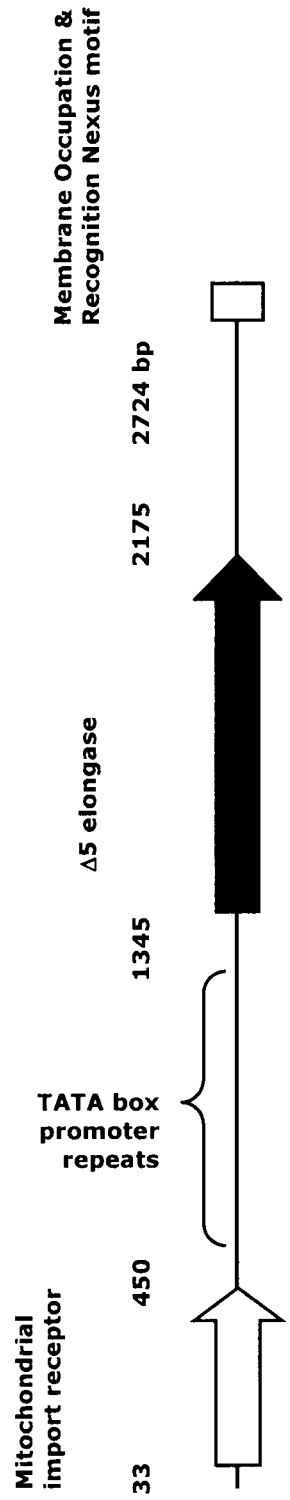
FIG. 4 shows a genetic outline schematic for the isolated D5 elongase.

Conversely, a BLASTX™ search identified the D5-elongase protein as having 89% identity to a *Thraustochytrium* sp. FJN-10 polyunsaturated fatty acid elongase. FIG. 2B shows a rooted neighbour joining phylogenetic tree, determined using CLUSTALX™, bootstrap analysis (1000×) using the results of a BLASTX™ search when compared to the ONC-T18 D5-elongase sequence. Further analysis determined that this 831 by long elongase, coding a 276 amino acid protein, contains four transmembrane regions specific to mitochondria, and one histidine box motif. The upstream component of this D5-elongase region comprises a single TATA box, multiple repeat regions and a promoter prior to a mitochondrial import receptor, while downstream the beginning of a membrane occupation and recognition nexus motif was identified (FIG. 4).

Characterisation of pYDes (Table 1) for both the n-3 and n-6 pathways, showed a 14% conversion of DPA n-3 or docosatetraenoic acid (DTA 22:4 n-6) to DHA or DPA n-6, respectively.

TABLE 1

D4-desaturase enzyme activity and characterisation

| Substrate | Product | % conversion average | stdev | (x) | With 0.01% ferric citrate % conversion | increase |
|---|---|---|---|---|---|---|
| DPA | DHA | 14.04 | 4.01 | 4 | 38.70 | 2.75 fold |
| DTA | DPA n-6 | 13.76 | 1.31 | 3 | 33.43 | 2.43 fold |
| DGLA | ARA | 0.87 | 0.27 | 3 | | |

When fed the corresponding D4-desaturase substrate dihomo-g-linolenic acid (DGLA, 20:3 n-6), no conversion was detected. In an effort to increase pYDes activity, trace metals such as ferric citrate was added to the media, resulting in an increase in DPA to DHA conversion (Table 1). In contrast, presently pYElo shows minimal conversion when either EPA or arachidonic acid (ARA 20:4 n-6) were fed.

D4-desaturase and D5-elongase genes from the high fatty acid producing strain *Thraustochytrium* sp. ONC-T18, have been successfully isolated and cloned, followed by expression in *S. cerevisiae*.

Furthermore, the D4-desaturase enzyme was shown to convert both DPA or DTA to their respective end products both in their native form and via supplementation with trace metals. Feed studies with other fatty acids confirmed the D4 specific activity of this desaturase. Through the use of gene manipulation techniques, such as error-prone PCR, this activity will be further enhanced so as to effect an increase in production of DHA in our strain.

Disclosed are compositions comprising a D4 desaturase wherein the D4 desaturase has at least or greater than 70%, 80%, 89%, 90%, 95%, 96%, 97% identity to SEQ ID NO:26.

Also disclosed are compositions, wherein any change away from SEQ ID NO:26 is a conservative change.

Also disclosed are compositions comprising a nucleic acid wherein the nucleic acid encodes any of the D4 desaturase.

Also disclosed are compositions, further comprising a vector.

Also disclosed are compositions comprising a cell wherein the cell comprises an of the compositions.

Also disclosed are compositions, wherein the cell is a eukaryote, a prokaryote, a *Thraustochytrid*, a yeast, or an *e coli*.

Also disclosed are compositions comprising a non-human animal wherein the non-human animal comprises any of the compositions.

Also disclosed are compositions, wherein the composition produces more polyunsaturated fatty acids than the composition in the absence of the D4 desaturase.

Also disclosed are compositions, wherein the fatty acid is EPA or DHA.

Also disclosed are compositions, wherein the desaturase contains at least one histidine box.

Also disclosed are compositions, wherein the desaturase contains at least 2 histidine boxes.

Also disclosed are compositions, wherein the desaturase contains at least three three histidine boxes.

Also disclosed are compositions, wherein the histidine box comprises the sequence HXXHH (SEQ ID NO:27) where X is any amino acid.

Also disclosed are compositions, wherein the histidine box comprises the sequence QXXHH (SEQ ID NO:28).

Also disclosed are compositions, wherein the desaturase also comprises a cytochrome b5 domain.

Also disclosed are compositions, wherein the cytochrome b5 domain resides at the 5'-end.

Also disclosed are compositions, wherein the desaturase is in the presence of a desaturase substrate Also disclosed are compositions, wherein the substrate has a concentration of at least 100 μM, 200 μM, 300 μM, 400 μM, 500 μM, 600 μM, 700 μM, 800 μM, 900 μM, or 1000 μM.

Also disclosed are compositions, wherein the substrate is Docosapentaenoic acid (22:5n-3), Docosatetraenoic acid (22:4n-6), or Dihomo-gamma-linolenic acid (20:3n-6).

Also disclosed are compositions, wherein the desaturase converts at least 0.1%, 0.5%, 1%, 5%, 10%, 30%, 50%, 70%, 90%, 95% of the available substrate.

Also disclosed are compositions, wherein the desaturase converts the amount of substrate shown in Table 1.

Also disclosed are compositions, wherein the composition is isolated.

Also disclosed are compositions comprising a D5 elongase wherein the D5 elongase has at least or greater than 70%, 80%, 89%, 90%, 95%, 96%, 97% identity to SEQ ID NO:15.

Also disclosed are compositions, wherein any change away from SEQ ID NO:15 is a conservative change.

Also disclosed are compositions comprising a nucleic acid wherein the nucleic acid encodes any of the D5 elongases.

Also disclosed are compositions encoding elongases or desaturases, further comprising a vector.

Also disclosed are compositions wherein the composition produces more polyunsaturated fatty acids than the composition in the absence of the D5 elongase, such as DHA or EPA.

Also disclosed are compositions wherein the elongase is in the presence of an elongase substrate Also disclosed are compositions, wherein the substrate is Eicosapentaenoic acid (20:5n-3) or Arachidonic acid (20:4n-6).

Also disclosed are compositions, wherein the elongase converts at least 0.1%, 0.5%, 1%, 5%, 10%, 30%, 50%, 70%, 90%, 95% of the available substrate.

Also disclosed are compositions, wherein the composition is isolated.

Also disclosed are compositions comprising any of the disclosed desaturase compositions and any of the disclosed elongase compositions.

Also disclosed are methods for producing a polyunsaturated fatty acid comprising using one or more of any of the compositions.

Also disclosed are methods, wherein the fatty acid produced is either EPA or DHA.

Also disclosed are methods of producing the compositions comprising isolating any of the compositions.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Nucleic Acids

There are a variety of molecules disclosed herein that are nucleic acid based, including for example the nucleic acids that encode, for example, the isolated D4 desaturase and D5 elongase as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, the isolated D4 desaturase and D5 elongase as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of the isolated D4 desaturase and D5 elongase or the genomic DNA of the isolated D4 desaturase and D5 elongase or they can interact with the polypeptide or fragments of the isolated D4 desaturase and D5 elongase. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of the isolated D4 desaturase and D5 elongase aptamers, the background protein could be serum albumin. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci.* USA 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

4. Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods.

As one example, if the antibody-encoding nucleic acid is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A.R. Gennaro, Mack Publishing Company, Easton, Pa. 1995.

5. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

6. Peptides a) Protein Variants

As discussed herein there are numerous variants of the the isolated D4 desaturase and D5 elongase proteins that are known and herein contemplated. In addition, to the known functional the isolated D4 desaturase and D5 elongase strain variants there are derivatives of the isolated D4 desaturase and D5 elongase proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 2 and 3 and are referred to as conservative substitutions.

Substantial changes in function or immunological identity are made by selecting substitutions that are less conservative than those in Table 3, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

TABLE 2

Amino Acid Abbreviations

| Amino Acid | Abbreviations | |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | K |
| glycine | Gly | G |
| histidine | His | H |
| isoleucine | Ile | I |

TABLE 2-continued

Amino Acid Abbreviations

| Amino Acid | Abbreviations | |
|---|---|---|
| leucine | Leu | L |
| lysine | Lys | K |
| phenylalanine | Phe | F |
| proline | Pro | P |
| serine | Ser | S |
| threonine | Thr | T |
| tyrosine | Tyr | Y |
| tryptophan | Trp | W |
| valine | Val | V |
| methionine | Met | M |

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

TABLE 3

Amino Acid Substitutions
Original Residue Exemplary Conservative
Substitutions, others are known in the art.

Ala; ser
Arg; lys, gln
Asn; gln; his
Asp; glu
Cys; ser
Gln; asn, lys
Glu; asp
Gly; pro
His; asn; gln
Ile; leu; val
Leu; ile; val
Lys; arg; gln;
Met; Leu; ile
Phe; met; leu; tyr
Ser; thr
Thr; ser
Trp; tyr
Tyr; trp; phe
Val; ile; leu Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 15 sets forth a particular sequence of a D5 elongase and SEQ ID NO:26 sets forth a particular sequence of a D4 desaturase protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level. Specifically disclosed are sequences having greater than 96% identity and 89% identity to SEQ ID NOs: 15 and 26.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:15 is set forth in SEQ ID NO:14. It is also understood that while no amino acid sequence indicates what particular DNA sequence encodes that protein within an organism, where particular variants of a disclosed protein are disclosed herein, the known nucleic acid sequence that encodes that protein in the particular strain from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 2 and Table 3. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $-CH_2NH-$, $-CH_2S-$, $-CH_2-CH_2-$, $-CH=CH-$ (cis and trans), $-COCH_2-$, $-CH(OH)CH_2-$, and $-CHH_2SO-$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($-CH_2NH-$, $CH_2CH_2-$); Spatola et al. Life Sci 38:1243-1249 (1986) ($-CH\,H_2-S$); Hann J. Chem. Soc Perkin Trans. I 307-314 (1982) ($-CH=CH-$, cis and trans); Almquist et al. J. Med. Chem. 23:1392-1398 (1980) ($-COCH_2-$); Jennings-White et al. Tetrahedron Lett 23:2533 (1982) ($-COCH_2-$); Szelke et al. European Appln, EP 45665 CA (1982): 97:39405 (1982) ($-CH(OH)CH_2-$); Holladay et al. Tetrahedron. Lett 24:4401-4404 (1983) ($-C(OH)CH_2-$); and Hruby Life Sci 31:189-199 (1982) ($-CH_2-S-$); each of which is incorporated herein by reference. A particularly preferred non-peptide linkage is $-CH_2NH-$. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

7. Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the isolated D4 desaturases and D5 elongases such that they can be identified, bound, purified, or have altered activity. Antibodies that bind the disclosed regions of the D4 desaturases and D5 elongases are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

(2) Human Antibodies

The disclosed human antibodies can be prepared using any technique. Examples of techniques for human monoclonal antibody production include those described by Cole et al. (*Monoclonal Antibodies and Cancer Therapy,* Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The antibodies and antibody fragments can also be administered to patients or subjects or cells as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A.R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Other molecules that interact with the isolated D4 desaturases and D5 elongases which do not have a specific pharmaceutical function, but which may be used for tracking changes within cellular chromosomes or for the delivery of diagnostic tools for example can be delivered in ways similar to those described for the pharmaceutical products.

9. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

10. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

11. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein can be used as targets for the combinatorial approaches. Also disclosed are the compositions that are identified through combinatorial techniques or screening techniques in which the compositions disclosed in for example SEQ ID NOS:14, 15, 25, or 26 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, a fatty acid, are also disclosed. Thus, the products produced using the combinatorial or screening approaches that involve the disclosed compositions, such as, fatty acids, are also considered herein disclosed.

It is understood that the disclosed methods for identifying molecules that inhibit the interactions between, for example, the isolated D4 desaturases and the D5 elongases can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. *Proc. Natl. Acad. Sci. USA,* 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A peptide of choice, for example a portion of the isolated D4 desaturases or D5 elongases is attached to a DNA binding domain of a transcriptional activation protein, such as Gal 4. By performing the Two-hybrid technique on this type of system, molecules that bind the portion of the isolated D4 desaturases or D5 elongases can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxyamino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in iterative processes.

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, the isolated D4 desaturases or D5 elongases, are also disclosed. Thus, the products produced using the molecular modeling approaches that involve the disclosed compositions, such as, the isolated D4 desaturases or D5 elongases, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol._Toxiciol.* 29, 111-122; Perry and Davies, QSAR: Quantitative Structure-Activity Relationships in Drug Design pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

12. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

13. Compositions with Similar Functions

It is understood that the compositions disclosed herein have certain functions, such as enzymatic functions disclosed. Disclosed herein are certain structural requirements for performing the disclosed functions, and it is understood that there are a variety of structures which can perform the same function which are related to the disclosed structures, and that these structures will ultimately achieve the same result, for example stimulation or inhibition of the enzymatic function.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins, such as SEQ ID NO:23, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. *Science*, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett.* 307:97-101; Clark-Lewis I et al., J. Biol. Chem., 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (de Lisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. For example, disclosed are nucleic acids in SEQ ID NOs:14 and 25. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO:14 and 25, for example, and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO:14 and 25, for example, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO:14 and 25, for example, and a sequence controlling the expression of the nucleic acid.

Disclosed are nucleic acid molecules produced by the process comprising linking in an operative way a nucleic acid molecule comprising a sequence encoding a peptide set forth in SEQ ID NO:15 and 26, for example, and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:15 and 26, for example, and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO:15 and 26, for example, wherein any change from the SEQ ID NO:15 and 26, for example, are conservative changes and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Design of Degenerate Oligonucleotides for the Isolation of Desaturase and Elongase from Thraustochytrid ONC-T18

Analysis of the fatty acid composition of Thraustochytrid ONC-T18 revealed the presence of considerable amount of longer chain PUFA such as arachidonic acid (ARA, 20:4n-6), eicosapentaenoic acid (EPA, 20:5n-3), adrenic acid (ADA, 22:4n-6, ω6-docosapentaenoic acid (ω6-DPA, 22:5n-6), ω3-docosapentaenoic acid (ω3-DPAn-3), and docosahexaenoic acid (DHA, 22:6n-3). Thus it was thought that this organism contained an active Δ5-elongase capable of converting ARA to ADA or EPA to ω3-DPA and an active Δ4-desaturase which desaturates ADA to ω6-DPA or ω3-DPA to DHA (FIG. 1). The goal thus was to attempt to isolate these desaturase and elongase genes from Thraustochytrid ONC-T18, and eventually to verify the functionality by expression in an alternate host.

To isolate genes encoding functional desaturase enzymes, genomic DNA was extracted from the organism. Thraustochytrid ONC-T18 cultures were grown in a growth medium (5 g/l yeast extract, 5 g/l peptone, 40 g/l D(+)-glucose, 1.25 ml/l trace elements, 1.25 ml/l vitamins, 40 g/l sea salt; (trace elements: 5 g/l NaH2PO4.H$_2$O, 3.15 g/l FeCl3.6H2O, 4.36 g/l Na2EDTA.2H2O, 0.6125 mg/l CuSO4.5H2O, 0.0597 g/l Na2MoO4.2H2O, 0.022 g/l ZnSO4.7H2O, 0.01 g/l CoCl2.6H2O, 0.18 g/l MnCl2.4H2O, 13 µg/l H2SeO3, 2.7 mg/l NiSO4.6H2O, 1.84 mg/l Na$_3$VO4, 1.94 mg/l K2CrO4), (vitamins: 1 mg/l vitamin B12, 1 mg/l biotin, 0.20 g/l thiamine HCl)) at 26° C. for 16-20 hours with constant agitation. The cells were centrifuged 500 rpm, 5 min at room temperature in Sorvall Super T21 centrifuge with rotor ST-H750 using adapter Sorvall #00436, removed 80% of supernatant, resuspended cells in remaining medium and continued with extraction. Genomic DNA was isolated from cells using ULTRACLEAN® Microbial DNA Isolation kit (MO BIO Laboratories, Inc, Solana Beach, Calif.) as per manufacturer's protocol.

The approach taken was to design degenerate oligonucleotides (i.e., primers) that are conserved in known desaturases. These primers could be used in a PCR reaction to identify a fragment containing the conserved regions in the predicted desaturase genes from *Thraustochytrium*. Five sequences were available from *Thraustochytrium* sp., *Thraustochytrium aureum*, *Thraustochytrium* sp. ATCC 34304, *Thraustochytrium* sp. ATCC 21685, and *Thraustochytrium* sp. FJN-10 (EMBO accession number CS020087, Genbank accession number AF391546, AF391543, AF489589, DQ133575, respectively). The degenerate primers used were as follows using the Kodon primer designer software: Primer 4desat308 (Forward) (SEQ ID NO:1) 5'-GGRACAGCGASTTTTA-CAGGG-3', Primer 4desat1369 (Reverse) (SEQ ID NO:2) 5'-GTGCTCAATCTGGTGGTTKAG-3'.

The same approach was taken to design degenerate oligonucleotides (i.e., primers) that are conserved in known elongases. These primers could be used in a PCR reaction to identify a fragment containing the conserved regions in the predicted elongase genes from *Thraustochytrium* sp. Two sequences were available from *Thraustochytrium* sp. and *Thraustochytrium aureum* (EMBO accession number CS160897 and CS160879, respectively). The degenerate primers used were as follows using Kodon primer designer software: Primer 5elo202F (Forward) (SEQ ID NO:3) 5'-AAGCCYTTCGAGCTCAAGTYC-3', Primer 5elo768R (Reverse) (SEQ ID NO:4) 5'-GCACGAARAAGTTGC-CGAAG-3'. The degeneracy code for the oligonucleotide sequences was: K=G,T, R=A,G, S=G,C, Y=C,T.

2. Example 2

Isolation of Δ5-Elongase Nucleotide Sequences from *Thraustochytrium* sp. ONC-T18

To isolate the Δ5-elongase gene, PCR amplification was carried out in a 50 µl volume containing: 200 ng *Thraus-* tochytrium sp. ONC-T18 genomic DNA, 10 μl betaine, 10 mM Tris-HCl, pH 8.3, 50 mM KCl, 1.5 mM MgCl2, 0.001% gelatin, 200 μM each deoxyribonucleotide triphosphate, 1 μM of each primer and 0.2 unit of Taq DNA Polymerase (Sigma, Oakville, Ontario). Thermocycling was carried out at an annealing temperature of 55.7° C., the PCR reaction was resolved on a 0.8% low melt agarose gel, and the band of ~600 by was gel purified. PCR product was eluted from agarose with water and then purified with QIAquick PCR Purification kit (Qiagen, Valencia, Calif.). These DNA fragments were cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. One clone was thus isolated that showed sequence homology to previously identified Δ5-elongase. This clone is described as follows: Clone #600-16 (SEQ ID NO:5) was sequenced and the deduced amino acid sequence from 593 by showed 95% identity with polyunsaturated fatty acid elongase 1 *Thraustochytrium* sp. FJN-10 as the highest scoring match in a BLAST BLASTXT™ search.

To isolate the 3'-end, genome walking was carried out using APAGENE™ GOLD Genome Walking kit (BIO S&T, Montreal, Quebec) as per manufacturer's protocol, using genomic DNA purified from *Thraustochytrium* sp. ONC-T18, and oligonucleotides 3'GSPa (SEQ ID NO:6) (5'-CGCT-GCGCCCGTACATTACTACCATCCA-3') and 3'GSPb (SEQ ID NO:7) (5'-GTCGTCCAGTCCGTCTATGAC-3'). Both oligonucleotides were designed based on the #600-16 fragment of the putative Δ5-elongase. The PCR fragments were resolved on 0.8% low melt agarose gel, and the bands of ~500 to 2000 by were gel purified. PCR products were eluted from agarose with water and then purified with QIAquick PCR Purification kit (Qiagen, Valencia, Calif.). These DNA fragments were cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. Clone 3'C2-1 (SEQ ID NO:8) contained a 358 by insert which was identified to contain the 3'-end of the putative Δ5-elongase gene based on sequence homology with known 45-elongase and the presence of the 'TGA' stop codon.

To isolate the 5'-end, genome walking was carried out using APAGENE™ GOLD Genome Walking kit (BIO S&T, Montreal, Quebec) as per manufacturer's protocol, using genomic DNA purified from *Thraustochytrium* sp. ONC-T18, and oligonucleotides 5'GSPa (SEQ ID NO:9) (5'-CTCGGCACCCTTCTCCATCGGGTTGCCA-3') and 5'GSPb (SEQ ID NO:10) (5'-GTTGCCAAAGAGCTTG-TAGCCGCCGA-3'). Both oligonucleotides were designed based on the #600-16 fragment of the putative Δ5-elongase. The PCR fragments were resolved on 0.8% low melt agarose gel, and the bands of ~500 to 2000 by were gel purified. PCR products were eluted from agarose with water and then purified with QIAquick PCR Purification kit (Qiagen, Valencia, Calif.). These DNA fragments were cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. Clone 5'D2-11 (SEQ ID NO:11) was thus obtained that contained a 519 by insert that contained the putative 'ATG' start site of the novel Δ5-elongase. The deduced amino acid sequence of this fragment, when aligned with known Δ5-elongase showed 89% identity.

This Δ5-elongase gene was isolated in its entirety by PCR amplification using, the *Thraustochytrium* ONC-T18 genomic DNA as a template, and the following oligonucleotides: ONC-T18elo1 (Forward) (SEQ ID NO:12) 5'-GCT-GATGATGGCCGGGACC-3', ONC-T18elo1099 (Reverse) (SEQ ID NO:13) 5'-GGTCCACTCGAATTCGTAGCG-3'.

PCR amplification was carried out using in a 50 μl volume: 100 ng of the *Thraustochytrium* ONC-T18 genomic DNA, 25 mM TAPS-HCl, pH 9.3, 50 mM KCl, 2 mM MgCl$_2$, 1 mM β-mercaptoethanol, 1.5 μl DMSO, 200 μM each deoxyribonucleotide triphosphate, 0.5 μM of each primer and 1 unit PHUSION® high-fidelity DNA polymerase (Finnzymes, Espoo, Finland). Thermocycling conditions were as follows: the template was initially denatured at 98° C. for 30 sec, followed by 30 cycles of [98° C. for 10 sec, 62° C. for 30 sec, 72° C. for 30 sec], and finally an extension cycle at 72° C. for 5 minutes. The PCR product thus obtained was cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. The plasmid was purified using ULTRA-CLEAN® 6 Minute Mini Plasmid Prep kit (MO BIO Laboratories, Inc, Solana Beach, Calif.). The plasmid thus obtained was digested with BamHI/NotI and cloned into the yeast expression vector pYES2 (Invitrogen, Carlsbad, Calif.) to generate clone pYElo which was then used for expression studies.

The Δ5-elongase full-length gene insert was 1099 bp (SEQ ID NO:14) in length and, beginning with the first ATG, contained an 831 bp open reading frame encoding 276 amino acids. The amino acid sequence of the full-length gene (SEQ ID NO:15) contained regions of homology to Δ5-elongase from *Thraustochytrium* sp. FJN-10, *Marchantia polymorpha*, *Physcomitrella patens*, and *Mortierella alpina*.

3. Example 3

Isolation of Δ4-Desaturase Nucleotide Sequences from *Thraustochytrium* ONC-T18

To isolate the Δ4-desaturase gene, PCR amplification was carried out in a 50 μl volume containing: 100 ng *Thraustochytrium* ONC-T18 genomic DNA, 20 mM Tris-HCl, pH 8.4, 50 mM KCl, 2 mM MgCl$_2$, 400 μM each deoxyribonucleotide triphosphate, 2 μM of each primer and 0.1 unit Taq DNA Polymerase (Invitrogen, Carlsbad, Calif.). Thermocycling was carried out at an annealing temperature of 59.5° C., a portion of the PCR reaction was resolved on a 0.8% agarose gel, and the band of ~1100 bp was purified from the remaining PCR reaction with QIAquick PCR Purification kit (Qiagen, Valencia, Calif.). This DNA fragment was cloned into the TOPO TA Cloning kit for Sequencing (Invitrogen, Carlsbad, Calif.) as per manufacturer's specifications. The recombinant plasmid was transformed into TOP10 competent cells (Invitrogen, Carlsbad, Calif.), and clones were sequenced. One clone was thus isolated that showed sequence homology to previously identified Δ4-desaturase. This clone is described as follows: Clone #10-3 (SEQ ID NO:16) was sequenced and the deduced amino acid sequence from 967 bp showed 96% identity with delta-4 fatty acid desaturase *Thraustochytrium* sp. ATCC 21685 as the highest scoring match in a BLASTx search.

To isolate the 3'-end, genome walking was carried out using APAGENE™ GOLD Genome Walking kit (BIO S&T, Montreal, Quebec) as per manufacturer's protocol, using genomic DNA purified from *Thraustochytrium* ONC-T18, and oligonucleotides 4desat3'a (SEQ ID NO:17) (5'-TTACGCTTCCAAGGACGCGGTC-3') and 4desat3'b (SEQ ID NO:18) (5'-ATGAACAACACGCGCAAGGAGG-3'). Both oligonucleotides were designed based on the #10-3 fragment of the putative Δ4-desaturase. The PCR fragments were resolved on 0.8% low melt agarose gel, and the bands of ~500 to 2000 by were gel purified. PCR products were eluted from agarose with water and then purified with QIAquick PCR Purification kit (Qiagen, Valencia, Calif.). These DNA fragments were cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. Clone 3'D2-92 (SEQ ID NO:19) contained a 782 by insert which was identified to contain the 3'-end of the putative Δ4-desaturase gene based on sequence homology with known Δ4-desaturase and the presence of the 'TGA' stop codon.

To isolate the 5'-end, genome walking was carried out using APAGENE™ GOLD Genome Walking kit (BIO S&T, Montreal, Quebec) as per manufacturer's protocol, using genomic DNA purified from Thraustochytrium sp. ONC-T18, and oligonucleotides 4desat5' a (SEQ ID NO:20) (5'-CTGGATACACGTGCCCACGAAG-3') and 4desat5' b (SEQ ID NO:21) (5'-CACATCCAGTACAACGAGCTCCA-GAA-3'). Both oligonucleotides were designed based on the #10-3 fragment of the putative Δ4-desaturase. The PCR fragments were resolved on 0.8% low melt agarose gel, and the bands of ~500 to 2000 by were gel purified. PCR products were eluted from agarose with water and then purified with QIAquick PCR Purification kit (Qiagen, Valencia, Calif.). These DNA fragments were cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. Clone 5'-217 (SEQU ID NO:22) was thus obtained that contained a 946 by insert that contained the putative 'ATG' start site of the novel Δ4-desaturase. The deduced amino acid sequence of this fragment, when aligned with known Δ4-desaaturase showed 96% identity.

This Δ4-desaturase gene was isolated in its entirety by PCR amplification using, the Thraustochytrium sp. ONC-T18 genomic DNA as a template, and the following oligonucleotides: ONC-T184des380F (Forward) (SEQ ID NO:23) 5'-CGATTGAGAACCGCAAGCTTT-3', ONC-T184DES1687R (Reverse) (SEQ ID NO:24) 5'-GCAG-CACTGCTGTGCTCTGGT-3'.

PCR amplification was carried out using in a 50 μl volume: 300 ng of the Thraustochytrium ONC-T18 genomic DNA, 25 mM TAPS-HCl, pH 9.3, 50 mM KCl, 2 mM MgCl2, 1 mM β-mercaptoethanol, 1.5 μl DMSO, 200 μM each deoxyribonucleotide triphosphate, 0.5 μM of each primer and 1 unit PHUSION® high-fidelity DNA polymerase (Finnzymes, Espoo, Finland). Thermocycling conditions were as follows: the template was initially denatured at 98° C. for 30 sec, followed by 30 cycles of [98° C. for 10 sec, 61° C. for 30 sec, 72° C. for 30 sec], and finally an extension cycle at 72° C. for 5 minutes. The PCR product thus obtained was cloned into the pT7Blue-3 PERFECTLY BLUNT® Cloning kit (Novagen, San Diego, Calif.) as per manufacturer's specifications. The recombinant plasmids were transformed into NovaBlue competent cells (Novagen, San Diego, Calif.), and clones were sequenced. The plasmid was purified using ULTRA-CLEAN® 6 Minute Mini Plasmid Prep kit (MO BIO Laboratories, Inc, Solana Beach, Calif.). The plasmid thus obtained was digested with BamHI/NotI and cloned into the yeast expression vector pYES2 (Invitrogen, Carlsbad, Calif.) to generate clone pYDes which was then used for expression studies.

The Δ4-desaturase full-length gene insert was 1757 by (SEQ ID NO:25) in length and, beginning with the first ATG, contained an 1509 by open reading frame encoding 519 amino acids. The amino acid sequence of the full-length gene (SEQ ID NO:26) contained regions of homology to Δ4-desaturase from Thraustochytrium sp. ATCC21685, Thraustochytrium sp. FJN-10, and Thraustochytrium aureum. It also contained the three conserved 'histidine boxes' found in all known membrane-bound desaturases. (Okuley, et al. (1994) The Plant Cell 6:147-158). These were present at amino acid 181-185, 217-222 and 454-458. As with other membrane-bound Δ4-desaturases, the third Histidine-box motif (HXXHH, SEQ ID NO:27) in Thraustochytrium ONC-T18 Δ4-desaturase was found to be QXXHH (SEQ ID NO:28). This sequence also contained a cytochrome b5 domain at the 5'-end. This cytochrome is thought to function as an electron donor in these enzymes.

4. Example 4

Expression of Thraustochytrium ONC-T18 Δ4-Desaturase and Δ5-Elongase Genes in Yeast Clone pYDes, which consisted of the full length Δ4-desaturase cloned into pYES2 (Invitrogen, Carlsbad, Calif.), and clone pYElo, which consisted of the full-length Δ5-elongase gene in pYES2, were transformed into competent Saccharomyces cerevisiae INVSc1. Yeast transformation was carried out using the S. c. EasyComp Transformation kit (Invitrogen, Carlsbad, Calif.) according to conditions specified by the manufacturer. Transformants were selected for uracil auxotrophy on media lacking uracil (SC-Ura). To detect the specific desaturase activity of these clones, transformants were grown in the presence of 500 μM specific fatty acid substrates as listed below: A) Docosapentaenoic acid (22:5n-3) (conversion to docosahexaenoic acid would indicate Δ4-desaturase activity), B) Docosatetraenoic acid (22:4n-6) (conversion to docosapentaenoic acid (22:5n-6) would indicate Δ4-desaturase activity), C) Dihomo-gamma-linolenic acid (20:3n-6) (conversion to arachidonic acid (20:4n-6) would indicate Δ5-desaturase activity), D) Eicosapentaenoic acid (20:5n-3) (conversion to docosapentaenoic acid (22:5n-3) would indicate Δ5-elongase activity), E) Arachidonic acid (20:4n-6) (conversion to docosatetraenoic acid (22:4n-6) would indicate Δ5-elongase activity).

The negative control strain was INVSc1 containing the unaltered pYES2 vector, and these were grown simultaneously. The cultures were vigorously agitated (150 rpm) and grown for 96 hours at 20° C. in the presence of 500 μM (final concentration) of the various substrates. The cells were pelleted and washed in 100 mM phosphate buffer, pH 7.0, cell pellets were freeze dried. The lipids were then extracted and derivitized to fatty acid methyl esters (FAME) for gas chromatography analysis (GC). Transesterification and extraction was done using 100 mg freeze dried cells, with C19:0 as internal standard, added transesterification reaction mix (methanol: hydrochloric acid: chloroform, 10:1:1) mixed and heated at 90° C. for 2 hours, then allowed to cool at room temperature. FAMEs were extracted by adding 1 ml water, and 2 ml hexane: chloroform (4:1), and allow organic and aqueous phases to separate. The organic layer was extracted and treated with 0.5 g of anhydrous sodium sulfate to remove particulates and residual water. The organic solvents were evaporated under a stream of argon. The FAMEs were resuspended in iso-octane and analysed by GC-FID. The percent conversion was calculated by dividing the product produced by the sum of (the product produced+the substrate added) and then multiplying by 100. Table 4 represents the enzyme activity of the genes isolated based on the percent conversion of substrate added.

TABLE 4

Δ4-desaturase enzyme activity and characterization.

| Vector | Substrate | Product | % conversion average | stdev | |
|---|---|---|---|---|---|
| pYES2 | C22:5 n-3 | C22:6 n-3 | 0.07 | 0.14 | x = 4 |
| pYDes | | | 14.04 | 4.01 | |
| pYES2 | C22:4 n-6 | C22:5 n-6 | 0.53 | 0.92 | x = 3 |
| pYDes | | | 13.76 | 1.31 | |
| pYES2 | C20:3 n-6 | C20:4 n-6 | 0.42 | 0.37 | x = 3 |
| pYDes | | | 0.87 | 0.27 | |

The pYDes clone that contained the Δ4-desaturase gene from *Thraustochytrium* ONC-T18 converted 14% of the 22:5n-3 substrate to 22:6n-3, as well as 14% of the 22:4n-6 substrate to 22:5n-6. This confirms that the gene encodes a Δ4-desaturase. There was no background (non-specific conversion of substrate) in this case.

5. Example 5

Manipulation of ONC-T18 Δ4-Desaturase Activity with Ferric Citrate

Clone pYDes, which consisted of the full length Δ4-desaturase cloned into pYES2 (Invitrogen, Carlsbad, Calif.), was transformed into competent *Saccharomyces cerevisiae* INVSc1. The negative control strain was INVSc1 containing the unaltered pYES2 vector, and these were grown simultaneously. The cultures were vigorously agitated (150 RPM) and grown for 96 hours at 20° C. in the presence of 500 μM (final concentration) of DPA and 0.01% ferric citrate. The cells were then treated as described previously to determine the percent conversion of DPA to DHA. The percent conversion, in the presence of ferric citrate was 38.70%, in this case a 2.75 fold increase of Δ4-desaturase activity.

What is claimed is:

1. A composition comprising an isolated D4 desaturase, wherein the D4 desaturase has at least 98% sequence identity to SEQ ID NO:26 and wherein the desaturase activity is retained.

2. The composition of claim 1, wherein the isolated D4 desaturase has conservative changes.

3. A composition comprising an isolated nucleic acid, wherein the nucleic acid encodes the D4 desaturase of claim 1.

4. The composition of claim 3, further comprising a vector.

5. An isolated cell, wherein the cell comprises the composition of claim 1.

6. The cell of claim 5, wherein the cell is a plant or non-human animal cell.

7. The cell of claim 5, wherein the cell is a *Thraustochytrid*, a yeast, or an *Escherichia coli*.

8. The composition of claim 1, wherein the composition produces more polyunsaturated fatty acids than the composition in the absence of the D4 desaturase.

9. The composition of claim 8, wherein the fatty acid is Eicosapentaenoic acid (EPA) or Docosahexaenoic acid (DHA).

10. The composition of claim 1, wherein the desaturase contains at least one histidine box.

11. The composition of claim 10, wherein the histidine box comprises the sequence HXXHH (SEQ ID NO:27), wherein X is any amino acid.

12. The composition of claim 10, wherein the histidine box comprises SEQ ID NO:28.

13. The composition of claim 10, wherein the desaturase also comprises a cytochrome b5 domain.

14. The composition of claim 13, wherein the cytochrome b5 domain resides at the N-terminal end.

15. A method for producing a polyunsaturated fatty acid comprising: culturing a cell comprising an isolated D4 desaturase in a suitable nutrient medium, wherein the D4 desaturase has at least 98% sequence identity to SEQ ID NO:26.

16. The method of claim 15, wherein the fatty acid produced is ARA, EPA or DHA.

* * * * *